US010538579B2

(12) United States Patent
Maynard et al.

(10) Patent No.: US 10,538,579 B2
(45) Date of Patent: Jan. 21, 2020

(54) BISPECIFIC PERTUSSIS ANTIBODIES

(71) Applicant: BOARD OF REGENTS, THE UNIVERSITY OF TEXAS SYSTEM, Austin, TX (US)

(72) Inventors: Jennifer Maynard, Austin, TX (US); Ellen Wagner, Larkspur, CO (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/677,092

(22) Filed: Aug. 15, 2017

(65) Prior Publication Data

US 2018/0118817 A1 May 3, 2018

Related U.S. Application Data

(60) Provisional application No. 62/375,344, filed on Aug. 15, 2016.

(51) Int. Cl.
*C07K 16/12* (2006.01)
*A61P 31/04* (2006.01)
*A61K 39/00* (2006.01)

(52) U.S. Cl.
CPC .......... *C07K 16/1225* (2013.01); *A61P 31/04* (2018.01); *A61K 2039/505* (2013.01); *C07K 2317/31* (2013.01); *C07K 2317/51* (2013.01); *C07K 2317/515* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,884,879 | B1 | 4/2005 | Baca et al. |
| 8,653,243 | B2 | 2/2014 | Maynard |
| 9,260,510 | B2 | 2/2016 | Maynard |
| 9,512,204 | B2 | 12/2016 | Mavnard et al. |
| 10,035,846 | B2 | 7/2018 | Mavnard et al. |
| 2007/0237779 | A1 | 10/2007 | Ledbetter et al. |
| 2013/0272964 | A1 | 10/2013 | Dall'acqua et al. |
| 2014/0193401 | A1 | 7/2014 | Mavnard et al. |
| 2015/0353628 | A1 | 12/2015 | Mavnard et al. |
| 2016/0304588 | A1 | 10/2016 | Maynard |

FOREIGN PATENT DOCUMENTS

| | | | |
|---|---|---|---|
| EP | 0320866 | 6/1989 | |
| WO | WO-2015153685 A1 * | 10/2015 | ......... C07K 16/1225 |
| WO | WO 2018/035107 | 2/2018 | |

OTHER PUBLICATIONS

Vajdos et al. (J Mol Biol. Jul. 5, 2002;320(2):415-28 (Year: 2002).*
Brown et al. (J Immunol. May 1996;156(9):3285-91 (Year: 1996).*
"1B7" Product Information Sheet from NIBSC, NISBC code 99/506, dated Oct. 4, 2008.
"AbYsis Distribution Report for Kabat L65", printout from www.bioinf.org.uk/abysis/searches/distributions/distributions/html (last visited May 28, 2015).
Almagro, Juan C., and Johan Fransson. "Humanization of antibodies." *Front Biosci* 13.1 (2008): 1619-1633.
Antoine and Locht. "Roles of the disulfide bond and the carboxy-terminal region of the S1 subunit in the assembly and biosynthesis of pertussis toxin." *Infection and immunity* 58.6 (1990): 1518-1526.
Bartoloni. A., et al. "Mapping of a protective epitope of pertussis toxin by in vitro refolding of recombinant, fragments." *Nature Biotechnology* 6.6 (1988): 709.
Bruss, Jon B., and George R. Siber. "Protective effects of pertussis immunoglobulin (P-IGIV) in the aerosol challenge model." *Clinical and diagnostic laboratory immunology* 6.4 (1999): 464-470.
Bruns, Jon B., and George R. Siber. "Quantitative priming with inactivated pertussis toxoide vaccine in the aerosol challenge model." *Infection and immunity* 70.8 (2002): 4600-4608.
Bruss, Jon B., et al. "Treatment of severe pertussis: a study of the safety and pharmacology of intravenous pertussis immunoglobulin." *The Pediatric infectious disease journal* 18.6 (1999): 505-511.
Burnette, W. Neal, et al. "Pertussis toxin SI mutant with reduced enzyme activity and a conserved protective epitope." *Science* 242.4875 (1988): 72-74.
Cherry, James D., et al. "A search for serologic correlates of immunity to Bordetella pertussis cough illnesses." *Vaccine*16.20 (1998): 1901-1906.
Cieplak, Witold, et al. "Identification of a region in the S1 subunit of pertussis toxin that is required for enzymatic activity and that contributes to the formation of a neutralizing antigenic determinant." *Proceedings of the National Academy of Sciences* 85.13 (1988): 4667-4671.
Colman, Peter M. "Effects of amino acid sequence changes on antibody-antigen interactions." *Research in Immunology*145.1 (1994): 33-36.
Corada, Monica, et al. "Monoclonal antibodies directed to different regions of vascular endothelial cadherin extracellular domain affect adhesion and clustering of the protein and modulate endothelial permeability." *Blood* 97.6 (2001): 1679-1684.
Felici, Franco, et al. "Mimicking of discontinuous epitopes by phage-displayed peptides, II. Selection of clones recognized by a protective monoclonal antibody against the Bordetella pertussis toxin from phage peptide libraries." *Gene* 128.1 (1993): 21-27.
Granström, M., et al. "Specific immunoglobulin for treatment of whooping cough." *The Lancet* 338.8777 (1991): 1230-1233.
Hausman, Sally Z., and Drusilia L. Burns. "Use of Pertussis Toxin Encoded by ptxGenes from Bordetella bronchiseptica to Model the Effects of Antigenic Drift of Pertussis Toxin on Antibody Neutralization." *Infection and immunity* 68.6 (2000): 3763-3767.
Hazes, Bart, et al. "Crystal structure of the pertussis toxin-ATP Complex: A molecular sensor." *Journal of molecular biology* 258.4 (1996): 661-671.

(Continued)

*Primary Examiner* — Brian Gangle
(74) *Attorney, Agent, or Firm* — Parker Highlander PLLC

(57) ABSTRACT

The present invention relates, in part, to bispecific antibodies that bind the pertussis toxin protein. The present invention further relates to the use of the bispecific antibodies for the prevention and treatment of *Bordetella pertussis* infections.

10 Claims, 8 Drawing Sheets

Specification includes a Sequence Listing.

(56) References Cited

OTHER PUBLICATIONS

Hellwig, Sandra MM, et al. "Crucial role of antibodies to pertactin in Bordetella pertussis immunity." *The Journal of infectious diseases* 188.5 (2003): 738-742.
Houghten, et al., (Vaccines, 1986, Edited by Fred Brown: Cold Spring Harbor Laboratory).
International Search Report and Written Opinion issued in International Application No. PCT/US2017/046917, dated Feb. 13, 2018.
Jadhav, S. S., and S. Gairola. "Composition of acellular pertussis and combination vaccines: a general review." *Biologicals* 27.2 (1999): 105-110.
Kamachi, Kazunari, and Yoshichika krakawa. "Development of safer pertussis DNA vaccine expressing non-toxic C180 polypeptide of pertussis toxin S1 subunit." *Vaccine* 25.6 (2007): 1000-1006.
Kamachi, Kazunari, Toshifumi Konda, and Yoshichika Arakawa. "DNA vaccine encoding pertussis toxin S1 subunit induces protection against Bordetella pertussis in mice," *Vaccine* 21.31 (2003): 4609-4615.
Kaslow et al. "Detection of antibodies inhibiting the ADP-ribosyltransferase activity of pertussis toxin m human serum." *Journal of clinical microbiology* 30.6 (1992): 1380-4387.
Kenimer et al. "Monoclonal antibodies to pertussis toxin: utilization as probes of toxin function." *Hybridoma* 8.1 (1989): 37-51.
Kim, K. J., et al. "Epitopes on the S1 subunit of pertussis toxin recognized by monoclonal antibodies." *Infection and immunity*57.3 (1989): 944-950.
Kortemme, Tanja, and David Baker. "A simple physical model for binding energy hot spots in protein-protein complexes." *Proceedings of the National Academy of Sciences* 99.22 (2002): 14116-14121.
Kortemme, Tanja, David E. Kim, and David Baker. "Computationai alanine scanning of protein-protein interfaces." *Sci. STKE* 2004.219 (2004): p. 12-p. 12.
Krueger, Kathleen M., and Joseph T. Barbieri. "Assignment of functional domains involved in ADP-ribosylation and B-oligomer binding within the carboxyl terminus of the S1 subunit of pertussis toxin." *Infection and immunity* 62.5 (1994): 2071-2078.
Kwak, Ju-Won, and Chang-Soon Yoon. "A convenient method for epitope competition analysis of two monoclonal antibodies for their antigen binding." *Journal of immunological methods*191.1 (1996): 49-54.
Mayrose, Itay, et al. "Epitope mapping using combinatorial phage-display libraries: a graph-based algorithm." *Nucleic acids research* 35.1 (2006): 69-78.
Padlan, Eduardo A. "A possible procedure for reducing the immunogenicity of antibody variable domains while preserving their ligand-binding properties." *Molecular immunology* 28.4-5 (1991): 489-498.
Padlan, Eduardo A. "X-ray crystallography of antibodies." *Advances in protein chemistry* 49 (1996): 57-134.
Padlan, Eduardo A., C. Abergel, and J. P. Tipper. "Identification of specificity-determining residues in antibodies." *The FASEB journal* 9.1 (1995): 133-139.
Pai, Jennifer C., Jamie N. Sutherland, and Jennifer A. Maynard. "Progress towards recombinant anti-infective antibodies." *Recent patents on anti-infective drug discovery*4.1 (2009): 1-17.
Paul, 1993 Fundemental Immunology, Editor William Paul, 3$^{rd}$ ed, pp. 292-295 only.
Pizza, Mariagrazia, et al. "Mutants of pertussis toxin suitable for vaccine development." *Science* 246.4929 (1989): 497-500.
Pootong, Anek, et al. "Monoclonal antibody that neutralizes pertussis toxin activities." *Asian Pacific journal of allergy and immunology* 25.1 (2007): 37.
Raupach, Bärbel, and M. Alexander Schmidt. "Elucidation of linear epitopes of pertussis toxin using overlapping synthetic decapeptides: identification of a human B-cell determinant in the S1 subunit indicative of acute infections." *Microbial pathogenesis* 17.4 (1994): 213-226.
Rieber, Nikolaus, et al. "Differences of humoral and cellular immune response to an acellular pertussis booster in adolescents with a whole cell or acellular primary vaccination." *Vaccine* 26.52 (2008): 6929-6935.
Rudikoff, Stuart, et al. "Single amino acid substitution altering antigen-binding specificity." *Proceedings of the National Academy of Sciences* 79.6 (1982): 1979-1983.
Sato et al. "Monoclonal antibody against pertussis toxin: effect on toxin activity and pertussis infections." *Infection and immunity* 46.2 (1984): 422-428.
Sato, et al. "Comparison of pertussis toxin (PT)-neutralizing activities and mouse-protective activities of anti-PT mouse monoclonal antibodies." *Infection and immunity* 59.10 (1991): 3832-3835.
Sato, et al. "Effect of monoclonal antibody to pertussis toxin on toxin activity." *Infection and immunity* 55.4 (1987): 909-915.
Sato, et al. "Separation and purification of the hemagglutinins front Bordetella pertussis." *infection and immunity* 41.1 (1983): 313-320.
Sato, H., and Y. Sato. "Protective activities in mice of monoclonal antibodies against pertussis toxin." *Infection and immunity* 58.10 (1990): 3369-3374.
Smith, Michael J., et al. "Monoclonal antibody 11E10, which neutralizes shiga toxin type 2 (Stx2), recognizes three regions on the Stx2 a subunit, blocks the enzymatic action of the toxin in vitro, and alters the overall cellular distribution of the toxin." *Infection and immunity* 77.7 (2009): 2730-2740.
Storsaeter, Jann, et al. "Levels of anti-pertussis antibodies related to protection after household exposure to Bordetella pertussis." *Vaccine* 16.20 (1998): 1907-1916.
Sutherland, Jamie N., and Jennifer A. Maynard. "Characterization of a key neutralizing epitope on pertussis toxin recognized by monoclonal antibody 1B7." *Biochemistry*48.50 (2009): 11982-11993.
Wagner, Ellen K., et al. "Synergistic neutralization of pertussis toxin by a bispecific antibody in vitro and in vivo." *Clinical and Vaccine Immunology* (2016): CVI-00371.
Weiss, Alison A., et al. "Tn5-induced mutations affecting virulence factors of Bordetella pertussis." *Infection and Immunity* 42.1 (1983): 33-41.
Williamson, Peter, and Ruth Matthews. "Development of neutralising human recombinant antibodies to pertussis toxin." *FEMS Immunology & Medical Microbiology* 23.4 (1999): 313-319.
Witvliet, M. H., et al. "Binding of pertussis toxin to eucaryotic cells and glycoproteins." *Infection and immunity* 57.11 (1989): 3324-3330.

* cited by examiner

FIG. 1

```
                         221                                             231
            Glu Pro Lys Ser Cys Asp Lys Thr His Thr Cys Pro Pro Cys Pro Ala
                        Hinge.....................................|.....
            Pro Glu Leu Leu Gly Gly Pro Ser Val Phe Leu Phe Pro Pro Lys Pro
            ................................................................
            Lys Asp Thr Leu Met Ile Ser Arg Thr Pro Glu Val Thr Cys Val Val
            ................................................................
            Val Asp Val Ser His Glu Asp Pro Glu Val Lys Phe Asn Trp Tyr Val
            ....................................................CH2.....
            Asp Gly Val Glu Val His Asn Ala Lys Thr Lys Pro Arg Glu Glu Gln
            ................................................................
            Tyr Asn Ser Thr Tyr Arg Val Val Ser Val Leu Thr Val Leu His Gln
            ................................................................
            Asp Trp Leu Asn Gly Lys Glu Tyr Lys Cys Lys Val Ser Asn Lys Ala
            ................................................................
            Leu Pro Ala Pro Ile Glu Lys Thr Ile Ser Lys Ala Lys Gly Gln Pro
            .........................................|....................
            Arg Glu Pro Gln Val Tyr Thr Leu Pro Pro Ser Arg Glu Glu Met Thr
            ................................................................
            Lys Asn Gln Val Ser Leu Thr Cys Leu Val Lys Gly Phe Tyr Pro Ser
            ....................................................CH3.
            Asp Ile Ala Val Glu Trp Glu Ser Asn Gly Gln Pro Glu Asn Asn Tyr
            ................................................................
            Lys Thr Thr Pro Pro Val Leu Asp Ser Asp Gly Ser Phe Phe Leu Tyr
            ................................................................
            Ser Lys Leu Thr Val Asp Lys Ser Arg Trp Gln Gln Gly Asn Val Phe
            ................................................................
            Ser Cys Ser Val Met His Glu Ala Leu His Asn His Tyr Thr Gln Lys
            ................................................................
            Ser Leu Ser Leu Ser Pro Gly Lys
            ...............................|   (SEQ ID NO: 21)
```

FIGS. 2A-B
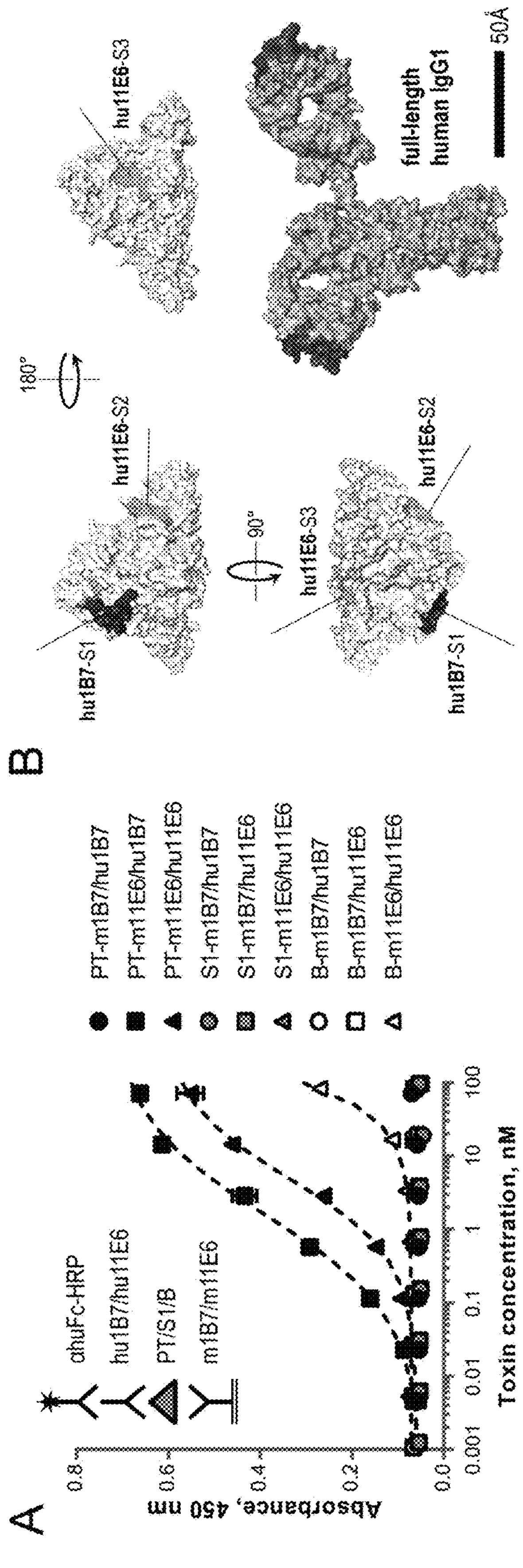

FIGS. 3A-C
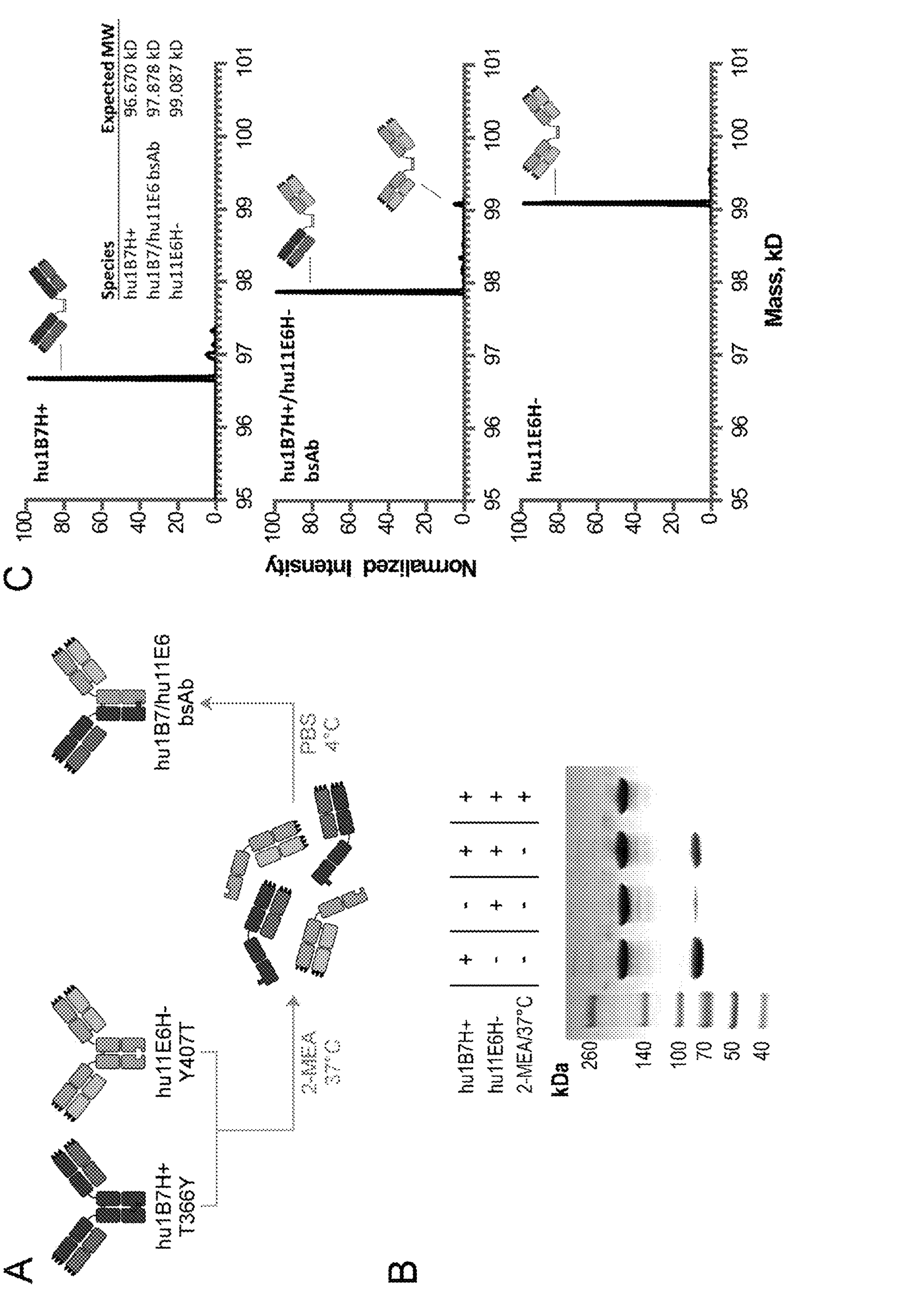

FIGS. 5A-C
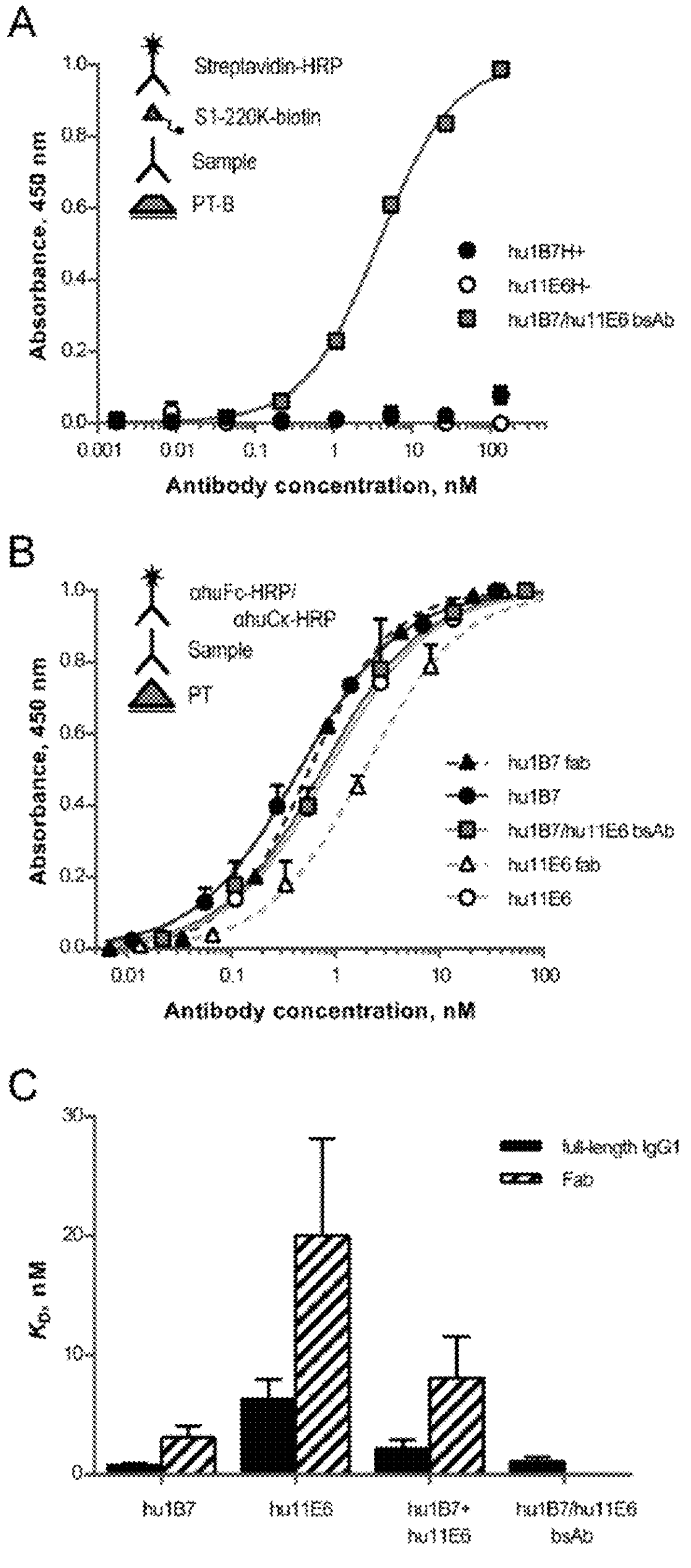

FIGS. 7A-B
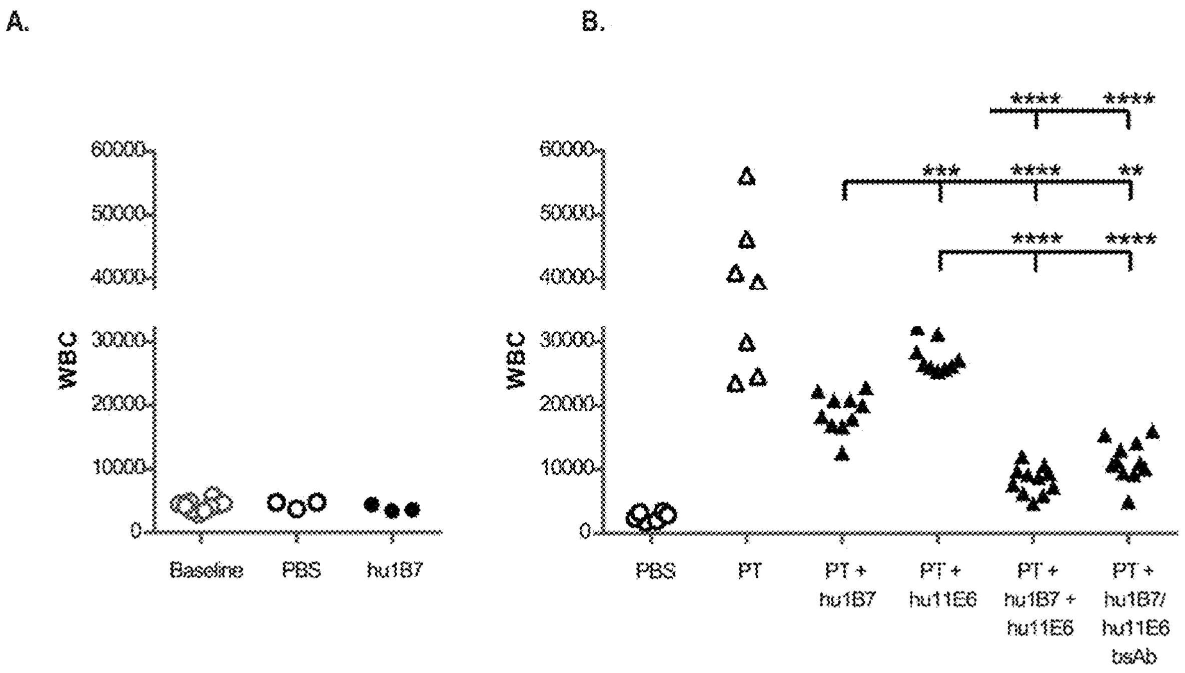

BISPECIFIC PERTUSSIS ANTIBODIES

This application claims the benefit of U.S. Provisional Patent Application No. 62/375,344, filed Aug. 15, 2016, the entirety of which is incorporated herein by reference.

FIELD OF THE INVENTION

The present invention relates, in part, to bispecific antibodies that bind the pertussis toxin protein. The present invention further relates to the use of the bispecific antibodies for the prevention and treatment of diseases including *Bordetella pertussis* infections.

BACKGROUND

Pertussis, or whooping cough, is an infection of the respiratory tract caused by the Gram-negative bacterium *Bordetella pertussis*. Pertussis infections are directly transmitted through the air and can cause respiratory complications (e.g., uncontrollable, violent coughing), nerve damage and high mortality, particularly in children of low socioeconomic groups and in new born babies without maternal, anti-pertussis antibodies. Infants with pertussis often require hospitalization in pediatric intensive care units, and their treatments involve mechanical ventilation. Pertussis in adults generally leads to a chronic cough referred to as the "cough of 100 days."

While antibiotic treatment can eliminate the *B. pertussis* bacteria from the respiratory tract, it does not neutralize the pertussis toxin (PT) protein, which is a major contributor to disease and is responsible for local and systemic disease symptoms including leukocytosis and immunosuppression. As such, antibiotic treatments often have minimal effects on the course of pertussis. In contrast, antibody therapy offers the advantage of specificity that antibiotic treatments may lack.

Antibodies that bind the pertussis toxin protein have been developed. In addition, antibody cocktails comprising different antibodies that bind the pertussis toxin protein have also been developed. However, such antibody cocktails and mixtures have the drawbacks of increased complexity and costs of manufacturing. For example, a binary mixture typically involves production and manufacturing of each antibody separately, with a final mixing step prior to fill/finish processing. Such methods are also susceptible to batch failure from each individual antibody. Additionally, antibody mixtures are subject to the same strict FDA approval processes as monoclonal preparations, and documentation for the safety of each individual component as well as the mixture is needed.

Accordingly, there remains a need for improved antibody-based agents against the pertussis toxin protein with increased efficacy and reduced side effects and which can be easily manufactured.

SUMMARY

In various aspects, the present invention is directed to bispecific antibodies that bind to and/or neutralize a pertussis toxin protein. In some embodiments, the present bispecific antibodies bind to the pertussis toxin protein with high affinity and have the advantage that smaller dosages and/or less frequent dosing are required in the therapeutic use of these antibodies. In some embodiments, the present bispecific antibodies provide increased stabilization and extended in vivo half-lives.

In various embodiments, the present bispecific antibody comprises an immunoglobulin heavy chain and light chain derived from a humanized 1B7 (hu1B7) antibody. In some embodiments, the immunoglobulin heavy chain derived from the humanized 1B7 antibody comprises an amino acid mutation at T366, numbered according to the EU index as in Kabat. An exemplary mutation is T366Y.

In various embodiments, the present bispecific antibody comprises an immunoglobulin heavy chain and light chain derived from a humanized 11E6 (hu11E6) antibody. In some embodiments, the immunoglobulin heavy chain derived from the humanized 11E6 antibody comprises an amino acid mutation at Y407, numbered according to the EU index as in Kabat. An exemplary mutation is Y407T.

In various embodiments, the bispecific antibodies of the invention comprises an IgG constant region that has one or more amino acid modifications which increase the affinity of the constant region or fragments thereof for the neonatal Fc receptor (FcRn). In some embodiments, the constant region is derived from IgG1. In some embodiments, the constant region is derived from human IgG1. In some embodiments, the bispecific antibodies comprise an FcRn binding fragment (e.g., Fc or hinge-Fc domain) of an IgG constant region. In various embodiments, the IgG constant region comprises one or more mutations at amino acid residue 252, 254, 256, 433, 434, or 436. As used herein, all residues of the IgG constant region are numbered according to Kabat et al. (Sequences of Proteins of Immunological Interest, U.S. Department of Health and Human Services, 1991, which is incorporated by reference herein in its entirety). In an embodiment, the IgG constant region includes a triple M252Y/S254T/T256E mutation. In another embodiment, the IgG constant region includes a triple H433K/N434F/Y436H mutation. In a further embodiment, the IgG constant region includes the M252Y/S254T/T256E and H433K/N434F/Y436H mutations.

In various embodiments, the present bispecific antibodies show improved specificity. In an embodiment, the bispecific antibody of the invention binds the pertussis toxin protein with a $K_D$ of less than about 3 nM or lower. In another embodiment, the bispecific antibody of the invention binds the pertussis toxin protein with a $K_D$ of less than about 1.5 nM or lower. Further, the present bispecific antibody exhibits an extended in vivo half-life in addition to improved specificity. In some embodiments, the present bispecific antibody also exhibits reduced immunogenicity.

In various embodiments, the present invention also provides nucleic acids, expression vectors, host cells, and methods for making the bispecific antibodies. The present invention also provides pharmaceutical compositions comprising the bispecific antibodies.

In one aspect, the method of the invention involves treating a patient with *Bordetella pertussis*, comprising administering to the patient the present bispecific antibody, or pharmaceutical compositions including the antibody. In an embodiment, the method includes administering to the patient the bispecific antibody, along with antimicrobial agents.

In a further embodiment, the method of the invention is directed to preventing *Bordetella pertussis* infection in a subject by administering to the subject the bispecific antibody, or pharmaceutical compositions including the antibody.

In various embodiments, the methods of treatment or prevention relate to infants.

In some embodiments, the method of the invention involves preventing the onset of pertussis by prophylactically administering the bispecific antibody, or pharmaceutical compositions including the antibody, to a subject, including an infant that has yet to be vaccinated (e.g. such as, for instance, whole-cell vaccines and acellular vaccines, inclusive of the vaccine in DTaP, and the like).

In one embodiment, the method of the invention comprises reducing white blood cell count in the patient. In another embodiment, the method of the invention comprises reducing the duration and/or the frequency of cough in the patient. In a further embodiment, the method of the invention comprises reducing the levels of the *Bordetella pertussis* in the nasopharynx and the lung of the patient. In another embodiment, the method of the invention neutralizes the pertussis toxin protein.

In another aspect, the method of the invention involves treating a patient with *Bordetella parapertussis*, comprising administering to the patient the present bispecific antibody, or pharmaceutical compositions including the antibody. In another aspect, the method of the invention is directed to preventing *Bordetella parapertussis* infection in a subject by administering to the subject the bispecific antibody, or pharmaceutical compositions including the antibody. Other aspects and embodiments of the invention will be apparent from the following detailed description and examples.

DESCRIPTION OF THE DRAWINGS

FIG. 1 shows the amino acid sequence of the human IgG1 hinge-Fc region containing a hinge region, CH2 domain, and CH3 domain. Kabat numbering is as shown.

FIGS. 2A-B show orientation and stoichiometry of the hu1B7 and hu11E6 epitopes. The humanized hu1B7 antibody binds a single well-defined epitope on the S1 subunit while the hu11E6 antibody binds two highly homologous epitopes of which one is present on the S2 subunit while the other is present on the S3 subunit. FIG. 2A shows that pertussis toxin (PT) can simultaneously engage antibodies binding the 1B7 and 11E6 epitopes. Shown is a sandwich ELISA in which one antibody is used to capture PT (solid icons) or just the A (S1-220K, grey icons) or B subunit (hollow icons), which is then detected by a second antibody. Tested antibody pairs include an m1B7 capture antibody with hu1B7 detection (m1B7/hu1B7; circles), m1B7 capture with hu11E6 detection (m1B7 hu11E6; squares), or m11E6 capture with hu11E6 detection (m11E6/hu11E6; triangles). Error shown is the standard deviation between two replicates. FIG. 2B shows the relative orientations of the hu1B7 and hu11E6 epitopes. The hu11B7 epitope and the two hu11E6 epitopes are indicated. The lines extending from the epitopes are normal to the average plane, approximating the angle at which a bound Fab would project A full length huIgG1 structure is shown for scale.

FIGS. 3A-C show production of bispecific hu1B7/hu11E6 antibody. FIG. 3A shows schematic overview of the process used to create the bispecific antibody. Single amino acid residue changes were introduced into the parent antibody Fc domains to create "knob" (T366Y; hu1B7H+) and "hole" (Y407T; hu11E6H−) variants, which were expressed and purified separately. An equimolar mixture of the two proteins was then subjected to a controlled reduction and re-oxidation reaction, resulting in efficient formation of the bi-specific antibody. FIG. 3B shows purity of the knob and hole variants and confirmation of 2-MEA activity was monitored by non-reducing SDS-PAGE. Samples shown are with (+) or without (−) hu1B7H+, hu11E6H−, or the 2-MEA red/ox step. FIG. 3C shows LC/MS analyses of the purified hu1B7$H^+$ and hu11E6$H^-$ variants and the bispecific antibody after 2-MEA red/ox. Proteins were digested with IdeS enzyme to yield $F(ab')_2$ fragments and PNGase to remove covalently attached sugars. LC/MS was used to determine the purity of the bispecific preparation.

FIG. 4A shows reducing and non-reducing SDS-PAGE that was performed on the full-length and fab formats of hu1B7 and hu11E6 as well as the bispecific to assess purity. 3 μg of protein was used per lane. FIG. 4B shows differential scanning fluorimetry was performed to determine the melting profile of full-length hu1B7 and hu11E6, the hu1B7 and hu11E6 Fabs and the hu1B7/hu11E6 bispecific antibody. Curves are averages of 3 replicates at 400 μg/ml.

FIGS. 5A-C show biochemical characterization of bispecific and parent antibodies. FIG. 5A shows the hu1B7/hu11E6 bsAb (grey squares) was assayed for bispecific binding using a sandwich ELISA Purified PT-B subunit was used to capture hu11E6 arms, followed by biotinylated S1-220K to detect the hu1B7 binding site. The monospecific parent antibodies, hu1B7H+(solid circles) and hu11E6H− (hollow circles) were used as controls. FIG. 5B shows results from a PT-binding ELISA which was used to confirm binding activity of all variants and controls. A PT-coated plate was incubated with dilutions of full-length hu1B7 or hu11E6, the hu1B7 or hu11E6 Fabs or hu1B7/hu11E6 bispecific. FIG. 5C shows results from a competition ELISA which was used to determine the solution-based equilibrium dissociation constant (KD) of all variants. Data shown for full length (solid bars) and Fab formats (striped bars). For all panels, error shown is standard deviation. The competition ELISA data is averaged from 6 replicates over 3 experiments.

FIGS. 7A-B show in vivo neutralization of PT-induced leukocytosis. FIG. 7A shows the baseline and day 4 white blood cell (WBC) counts for mice administered 200 μg purified hu1B7 or PBS. FIG. 7B shows the WBC counts for five week old female BALB/c mice four days after receiving PBS, 2 μg PT in PBS, or 2 μg PT plus 20 μg total antibody in PBS via a lateral tail vein injection. Whole blood was collected and CD45+ white blood cell (WBC) measured by flow cytometry. Hollow circles indicate the WBC recorded for PBS and PT-only treated control groups. Solid circles indicate antibody treated groups. Groups were compared using 1-way ANOVA and Tukey's test with statistically significant comparisons indicated. Statistical significance indicated as: $^{}p<0.01$, $^{*}p<0.001$ and $^{****}p<0.0001$.

DETAILED DESCRIPTION

Figure 4A:
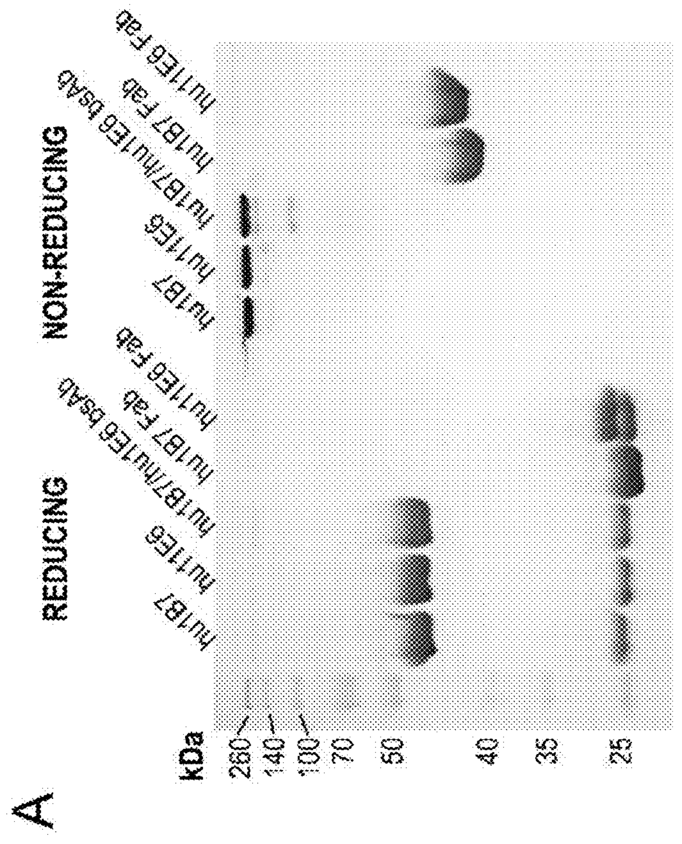
FIGS. 4A-B shows biophysical characterization of bispecific and parent antibodies.

The present invention is based, in part, on the discovery of bispecific antibodies that exhibit improved biological activities. Specifically, in some embodiments, the bispecific antibodies bind to the pertussis toxin protein and are useful for treating patients infected with the *Bordetella pertussis* bacteria. The disclosed antibodies are engineered to target the pertussis toxin protein with high specificity while exhibiting minimal immunogenicity thereby causing minimal side effects in patients. Furthermore, the disclosed antibodies exhibit enhanced stability and long in vivo half-lives. Various features and aspects of the invention are discussed in more detail below.

Bispecific Antibodies

In various aspects, the present invention is directed to one or more bispecific antibodies that bind to and/or neutralize a pertussis toxin protein.

In various embodiments, the bispecific antibodies of the invention comprise an immunoglobulin heavy chain and an immunoglobulin light chain derived from a humanized 1B7 antibody that binds a pertussis toxin protein. In various embodiments, the bispecific antibodies further comprises an immunoglobulin heavy chain and an immunoglobulin light chain derived from a humanized 11E6 antibody that binds a pertussis toxin protein. Exemplary humanized 1B7 and 11E6 antibodies are described in, for example, U.S. Patent Publication No. 2015/0353628, the entire disclosure of which is hereby incorporated by reference.

In various embodiments, the humanized 1B7 or 11E6 antibody is a non-human antibody that has been altered to increase its similarity to a human antibody. In some embodiments, the humanized antibody is a genetically engineered antibody in which at least one CDR (or functional fragment thereof) from a non-human, e.g. mouse, antibody ("donor antibody", which can also be rat, hamster or other non-human species) is grafted onto a human antibody ("acceptor antibody"). In some embodiments, more than one mouse CDR is grafted (e.g., all six mouse CDRs are grafted). The sequence of the acceptor antibody can be, for example, a mature human antibody sequence (or fragment thereof), a consensus sequence of a human antibody sequence (or fragment thereof), or a germline region sequence (or fragment thereof). Thus, in some embodiments, a modified humanized antibody may be an antibody having one or more CDRs from a donor antibody and variable region framework (FR). The FR may form part of a constant region within a human antibody.

In addition, in order to retain high binding affinity, amino acids in the human acceptor sequence may be replaced by the corresponding amino acids from the donor sequence, for example where: (1) the amino acid is in a CDR; (2) the amino acid is in the human framework region (e.g., the amino acid is immediately adjacent to one of the CDRs). See, U.S. Pat. Nos. 5,530,101 and 5,585,089, incorporated herein by reference, which provide detailed instructions for construction of humanized antibodies. Indeed, this selection of residues in, for example, the human framework region is often central to a humanized antibody's desirability. Although humanized antibodies often incorporate all six CDRs (e.g., as defined by Kabat, but often also including hypervariable loop H1 as defined by Chothia) from a mouse antibody, they can also be made with fewer mouse CDRs and/or less than the complete mouse CDR sequence (e.g. a functional fragment of a CDR).

In various embodiments, the bispecific antibodies comprise a humanized light chain variable region that is fused to a light chain constant region (e.g. human kappa or a lambda light chain). In various embodiments, the bispecific antibodies comprise a humanized heavy chain variable region that is fused to a heavy chain constant region, including various allotypes and isotypes of each. For example, the heavy chain constant region can be derived from any immunoglobulin type (e.g. IgG, IgM, IgA, IgD, or IgE). In some embodiments, IgG is used. For IgG, the constant region can come from IgG1, IgG2, IgG3, or IgG4. In some embodiments, IgG1 is used. In some embodiments, the IgG1 constant region comprises one or more mutations as described herein. Moreover, there are many isotypes of each IgG that can be chosen, some are naturally occurring and some are derivatives of naturally occurring isotypes. The type of IgG that is chosen will determine the effector functions of the antibody (e.g. opsonophagocytosis, complement fixation, etc.).

In various embodiments, the present bispecific antibody comprises an immunoglobulin heavy chain derived from a humanized 1B7 antibody. In some embodiments, the immunoglobulin heavy chain derived from the humanized 1B7 antibody comprises one or more of (e.g. 1, or 2, or 3 of):

a $CDR_{H1}$ comprising the amino acid sequence of: GYKFTSYWMH (SEQ ID NO: 1), a $CDR_{H2}$ comprising an amino acid sequence of: NIFPGSGSTNYAQKFQG (SEQ ID NO: 2), and a $CDR_{H3}$ comprising the amino acid sequence of: WLSGAYFDY (SEQ ID NO: 3).

In some embodiments, the immunoglobulin heavy chain derived from the humanized 1B7 antibody comprises an immunoglobulin heavy chain variable region comprising the amino acid sequence of:

```
                                         (SEQ ID NO: 4)
QVQLVQSGAEVKKPGASVKVSCKASGYKFTSYWMHWVRQAPGQGLEWIG

NIFPGSGSTNYAQKFQGRVTLTVDTSTSTAYMELSSLRSEDTAVYYCTR

WLSGAYFDYWGQGTTVTVSS
```

or variants thereof (e.g. with percent identities described elsewhere herein). In some embodiments, the immunoglobulin heavy chain derived from the humanized 1B7 antibody comprises an amino acid sequence of:

(SEQ ID NO 5)

<u>MGWSCIILFLVATATGVHS</u>QVQLVQSGAEVKKPGASVKVSCKASGYKFTS

YWMHWVRQAPGQGLEWIGNIFPGSGSTNYAQKFQGRVTLTVDTSTSTAYM

ELSSLRSEDTAVYYCTRWLSGAYFDYWGQGTTVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKRVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLYCLVKGFYPSDIAVE

WESNGQPENNYKTTPPVLDSDGSFFLYSKLTVDKSRWQQGNVFSCSVMHE

ALHNHYTQKSLSLSPGK or variants thereof (e.g. with percent identities described elsewhere herein). The amino acid sequence SEQ ID NO:5 described above includes a T366Y mutation as indicated in bold. In some embodiments, the immunoglobulin heavy chain derived from the humanized 1B7 antibody comprises the amino acid sequence of SEQ ID NO:5 but with a threonine at amino acid position 366. In some embodiments, the immunoglobulin heavy chain derived from the humanized 1B7 antibody comprises a C-terminal histidine tag (e.g., 6× His tag). In some embodiments, the immunoglobulin heavy chain derived from the humanized 1B7 antibody comprises the amino acid sequence of SEQ ID NO:5 but without the leader sequence as indicated above by underlining. In various embodiments, the present bispecific antibody further comprises an immunoglobulin light chain derived from a humanized 1B7 antibody. In some embodiments, the immunoglobulin light chain derived from the humanized 1B7 antibody comprises one or more of (e.g. 1, or 2, or 3 of):

a $CDR_{L1}$ comprising the amino acid sequence of: SASSSVSFMY (SEQ ID NO: 6), a $CDR_{L2}$ comprising an amino acid sequence of: LTSNLPS (SEQ ID NO: 7), and a $CDR_{L3}$ comprising the amino acid sequence of: QQWSSHPPT (SEQ ID NO: 8).

In some embodiments, the immunoglobulin light chain derived from the humanized 1B7 antibody comprises an immunoglobulin light chain variable region comprising the amino acid sequence of:

```
                                          (SEQ ID NO: 9)
QIVLIQSPATLSVSPGERVTLTCSASSSVSFMYWYQQKPGRAPKPLIY

LTSNLPSGVPARFSGSGSGTSYTLTINSLEAEDAATYYCQQWSSHPPTF

GSGTKLEIK
```

or variants thereof (e.g. with percent identities described elsewhere herein). In some embodiments, the immunoglobulin light chain derived from the humanized 1B7 antibody comprises an amino acid sequence of:

```
                                          (SEQ ID NO: 10)
MGWSCIILFLVATATGVHS QIVLTQSPATL SVSPGERVTL

TCSASSSVSF MYWYQQKPGR APKPLIYLTS NLPSGVPARF

SGSGSGTSYT LTINSLEAED AATYYCQQWS SHPPTFGSGT

KLEIKRTVAA PSVFIFPPSD EQLKSGTASV VCLLNNFYPR

EAKVQWKVDN ALQSGNSQES VTEQDSKDST YSLSSTLTLS

KADYEKHKVY ACEVTHQGLS SPVTKSFNRG EC
```

or variants thereof (e.g. with percent identities described elsewhere herein). In some embodiments, the immunoglobulin light chain derived from the humanized 1B7 antibody comprises the amino acid sequence of SEQ ID NO:10 but without the leader sequence as indicated above by underlining.

In various embodiments, the present bispecific antibodies comprise an immunoglobulin heavy chain derived from a humanized 1B7 antibody comprising an amino acid sequence having at least about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, about 90% identity, about 93% identity, about 95% identity, about 97% identity, about 98% identity, or about 99% identity to the entire heavy chain, the variable region, the complementarity determining regions, or the framework region sequence of SEQ ID NOs: 1-5.

In other embodiments, the bispecific antibody comprises an immunoglobulin light chain derived from a humanized 1B7 antibody comprising an amino acid sequence having at least about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, or about 90% identity to the entire heavy chain, the variable region, the complementarity determining regions, or the framework region sequence of SEQ ID NOs: 6-10.

In various embodiments, the present bispecific antibody comprises an immunoglobulin heavy chain derived from a humanized 11E6 antibody. In some embodiments, the immunoglobulin heavy chain derived from the humanized 11E6 antibody comprises on or more of (e.g. 1, or 2, or 3 of):

a $CDR_{H1}$ comprising the amino acid sequence of: GFTFTDYYVS (SEQ ID NO: 11), a $CDR_{H2}$ comprising an amino acid sequence of: FIRNKVNGYTTEFSSSVKG (SEQ ID NO: 12), and a $CDR_{H3}$ comprising the amino acid sequence of: VSYYGRGWYFDY (SEQ ID NO: 13).

In some embodiments, the immunoglobulin heavy chain derived from the humanized 11E6 antibody comprises an immunoglobulin heavy chain variable region comprising the amino acid sequence of:

```
                                          (SEQ ID NO: 14)
EVQVVESGGGLVQPGRSLRLSCTTSGFTFTDYYVSWVRQAPGKALEWLG

FIRNKVNGYTTEFSSSVKGRFTISRDNSKSILYLQMNSLKIEDTAVYYC

ARVSYYGRGWYFDYWGQGTTLTVSS
```

or variants thereof (e.g. with percent identities described elsewhere herein). In some embodiments, the immunoglobulin heavy chain derived from the humanized 11E6 antibody comprises an amino acid sequence of:

```
                                          (SEQ ID NO: 15)
MGWSCIILFLVATATGVHS EVQVVESGGGL VQPGRSLRLS

CTTSGFTFTD YYVSWVRQAP GKALEWLGFI RNKVNGYTTE

FSSSVKGRFT ISRDNSKSIL YLQMNSLKIE DTAVYYCARV

SYYGRGWYFD YWGQGTTLTV SSASTKGPSV FPLAPSSKST

SGGTAALGCL VKDYFPEPVT VSWNSGALTS GVHTFPAVLQ

SSGLYSLSSV VTVPSSSLGT QTYICNVNHK PSNTKVDKKV

EPKSCDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR EEMTKNQVSL TCLVKGFYPS
```

-continued

```
DIAVEWESNG QPENNYKTTP PVLDSDGSFF LTSKLTVDKS

RWQQGNVFSC SVMHEALHNH YTQKSLSLSP GK
```

or variants thereof (e.g. with percent identities described elsewhere herein). The amino acid sequence SEQ ID NO:15 described above includes a Y407T mutation as indicated in bold. In some embodiments, the immunoglobulin heavy chain derived from the humanized 11E6 antibody comprises the amino acid sequence of SEQ ID NO:15 but with a tyrosine at amino acid position 407. In some embodiments, the immunoglobulin heavy chain derived from the humanized 11E6 antibody comprises the amino acid sequence of SEQ ID NO:15 but does not include the C-terminal lysine residue. In some embodiments, the immunoglobulin heavy chain derived from the humanized 11E6 antibody comprises the amino acid sequence of SEQ ID NO:15 but without the leader sequence as indicated above by underlining. In various embodiments, the present bispecific antibody further comprises an immunoglobulin light chain derived from a humanized 11E6 antibody. In some embodiments, the immunoglobulin light chain derived from the humanized 11E6 antibody comprises one or more of (e.g. 1, or 2, or 3 of):

a $CDR_{L1}$ comprising the amino acid sequence of: RASQDIDNYLS (SEQ ID NO: 16), a $CDR_{L2}$ comprising an amino acid sequence of: YTSRLHS (SEQ ID NO: 17), and a $CDR_{L3}$ comprising the amino acid sequence of: QQGNTFPWT (SEQ ID NO: 18).

In some embodiments, the immunoglobulin light chain derived from the humanized 11E6 antibody comprises an immunoglobulin light chain variable region comprising the amino acid sequence of

```
                                            (SEQ ID NO: 19)
DIVMTQSESSLSASVGDRVTISCRASQDIDNYLSWFQQKPGGTVKLLIYY

TSRLHSGVPSRFSGSGSGTDYTLTISSLQPEDIATYFCQQGNTFPWTFGG

GTKLEIK
```

or variants thereof (e.g. with percent identities described elsewhere herein). In some embodiments, the immunoglobulin light chain derived from the humanized 11E6 antibody comprises an amino acid sequence of:

```
                                            (SEQ ID NO: 20)
MGWSCIILFLVATATGVHS D IVMTQSPSSL SASVGDRVTI

SCRASQDIDN YLSWFQQKPG GTVKLLIYYT SRLHSGVPSR

FSGSGSGTDY TLTISSLQPE DIATYFCQQG NTFPWTFGGG

TKLEIKRTVA APSVFIFPPS DEQLKSGTAS VVCLLNNFYP

REAKVQWKVD NALQSGNSQE SVTEQDSKDS TYSLSSTLTL

SKADYEKHKV YACEVTHQGL SSPVTKSFNR GEC
```

or variants thereof (e.g. with percent identities described elsewhere herein). In some embodiments, the immunoglobulin light chain derived from the humanized 11E6 antibody comprises the amino acid sequence of SEQ ID NO:20 but without the leader sequence as indicated above by underlining.

In various embodiments, the present bispecific antibodies comprise an immunoglobulin heavy chain derived from a humanized 11E6 antibody comprising an amino acid sequence having at least about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, about 90% identity, about 93% identity, about 95% identity, about 97% identity, about 98% identity, or about 99% identity to the entire heavy chain, the variable region, the complementarity determining regions, or the framework region sequence of SEQ ID NOs: 11-15.

In other embodiments, the bispecific antibody comprises an immunoglobulin light chain derived from a humanized 11E6 antibody comprising an amino acid sequence having at least about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, or about 90% identity to the entire heavy chain, the variable region, the complementarity determining regions, or the framework region sequence of SEQ ID NOs: 16-20.

Homology or identity may be determined in various ways that are within the skill in the art, for instance, using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87, 2264-2268; Altschul, (1993) J. Mol. Evol. 36, 290-300; Altschul et al., (1997) Nucleic Acids Res. 25, 3389-3402, incorporated by reference) are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases see Altschul et al., (1994) Nature Genetics 6, 119-129 which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992)

Proc. Natl. Acad. Sci. USA 89, 10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In various embodiments, it is contemplated herein that the immunoglobulin heavy and/or light chains, the heavy and/or light chain variable regions, the complementarity determining regions, and/or the framework region sequences may contain amino acid alterations (e.g., amino acid substitutions, deletions, or insertions) relative to SEQ ID NOs: 1-20.

In some embodiments, the immunoglobulin heavy chain and/or light chain variable sequences may contain from about 1 to about 50 mutations, from about 1 to about 40 mutations, from about 1 to about 35 mutations, from about 1 to about 30 mutations, about 1 to about 25 mutations, from about 1 to about 20 mutations, about 1 to about 15 mutations, or from about 1 to about 10 mutations independently selected from substitutions, deletions, or insertions with respect to SEQ ID NOs: 4, 9, 14 and 19. In various embodiments, the immunoglobulin heavy chain variable region sequences and/or light chain variable region sequences have about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, about 40 mutations, about 41 mutations, about 42 mutations, about 43 mutations, about 44 mutations, about 45 mutations, about 46 mutations, about 47 mutations, about 48 mutations, about 49 mutations, or about 50 mutations, relative to SEQ ID NOs: 4, 9, 14 and 19.

In some embodiments, the immunoglobulin heavy chain sequences may contain from about 1 to about 230 mutations, from about 1 to about 200 mutations, from about 1 to about 150 mutations, from about 1 to about 100 mutations, from about 1 to about 50 mutations, from about 1 to about 40 mutations, from about 1 to about 35 mutations, from about 1 to about 30 mutations, about 1 to about 25 mutations, from about 1 to about 20 mutations, about 1 to about 15 mutations, or from about 1 to about 10 mutations independently selected from substitutions, deletions, or insertions with respect to SEQ ID NOs: 5 and 15. In various embodiments, the immunoglobulin heavy chain sequences have about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, about 40 mutations, about 41 mutations, about 42 mutations, about 43 mutations, about 44 mutations, about 45 mutations, about 46 mutations, about 47 mutations, about 48 mutations, about 49 mutations, about 50 mutations, about 51 mutations, about 52 mutations, about 53 mutations, about 54 mutations, about 55 mutations, about 56 mutations, about 57 mutations, about 58 mutations, about 59 mutations, about 60 mutations, about 61 mutations, about 62 mutations, about 63 mutations, about 64 mutations, about 65 mutations, about 66 mutations, about 67 mutations, about 68 mutations, about 69 mutations, about 70 mutations, about 71 mutations, about 72 mutations, about 73 mutations, about 74 mutations, about 75 mutations, about 76 mutations, about 77 mutations, about 78 mutations, about 79 mutations, about 80 mutations, about 81 mutations, about 82 mutations, about 83 mutations, about 84 mutations, about 85 mutations, about 86 mutations, about 87 mutations, about 88 mutations, about 89 mutations, about 90 mutations, about 91 mutations, about 92 mutations, about 93 mutations, about 94 mutations, about 95 mutations, about 96 mutations, about 97 mutations, about 98 mutations, about 99 mutations, or about 100 mutations relative to SEQ ID NOs: 5 and 15.

In some embodiments, the immunoglobulin light chain sequences may contain from about 1 to about 120 mutations, from about 1 to about 100 mutations, from about 1 to about 90 mutations, from about 1 to about 80 mutations, from about 1 to about 70 mutations, from about 1 to about 50 mutations, from about 1 to about 40 mutations, from about 1 to about 35 mutations, from about 1 to about 30 mutations, about 1 to about 25 mutations, from about 1 to about 20 mutations, about 1 to about 15 mutations, or from about 1 to about 10 mutations independently selected from substitutions, deletions, or insertions with respect to SEQ ID NOs: 10 and 20. In various embodiments, the immunoglobulin light chain sequences have about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, about 40 mutations, about 41 mutations, about 42 mutations, about 43 mutations, about 44 mutations, about 45 mutations, about 46 mutations, about 47 mutations, about 48 mutations, about 49 mutations, about 50 mutations, about 51 mutations, about 52 mutations, about 53 mutations, about 54 mutations, about 55 mutations, about 56 mutations, about 57 mutations, about 58 mutations, about 59 mutations, about 60 mutations, about 61 mutations, about 62 mutations, about 63 mutations, about 64 mutations, about 65 mutations, about 66 mutations, about 67 mutations, about 68 mutations, about 69 mutations, about 70 mutations, about 71 mutations, about 72 mutations, about 73 mutations, about 74 mutations, about 75 mutations, about 76 mutations, about 77 mutations, about 78 mutations, about 79 mutations, about 80 mutations, about 81 mutations, about 82 mutations, about 83 mutations, about 84 mutations, about 85 mutations, about 86 mutations, about 87 mutations, about 88 mutations, about 89 mutations, about 90 mutations, about 91 mutations, about 92 mutations, about 93 mutations, about 94 mutations, about 95 mutations, about 96 mutations, about 97 mutations, about 98 mutations, about 99 mutations, or about 100 mutations relative to SEQ ID NOs: 10 and 20.

Illustrative amino acids that may be incorporated include a hydrophilic amino acid residue, which may include a polar and positively charged hydrophilic residue selected from arginine (R) and lysine (K), a polar and neutral of charge hydrophilic residue selected from asparagine (N), glutamine (Q), serine (S), threonine (T), proline (P), and cysteine (C), a polar and negatively charged hydrophilic residue selected from aspartate (D) and glutamate (E), or an aromatic, polar and positively charged hydrophilic including histidine (H); a hydrophobic amino acid residue which may include a hydrophobic, aliphatic amino acid selected from glycine (G), alanine (A), leucine (L), isoleucine (I), methionine (M), or valine (V) or a hydrophobic, aromatic amino acid selected from phenylalanine (F), tryptophan (W), or tyrosine (Y).

In various embodiments, the bispecific antibodies of the invention comprise heavy chains that are engineered to heterodimerize through the knobs-into-holes technology (Ridgway J B B, et. al. (1996) Protein Eng 1996; 9:617-21; the entire contents are hereby incorporated by reference). In some embodiments, mutations are introduced into the CH3 domains of the heavy chain derived from the humanized 1B7 antibody and the heavy chain derived from the humanized 11E6 antibody to modify the contact interface between the two heavy chains. In an embodiment, the heavy chain derived from the humanized 1B7 antibody is mutated such that amino acids with large side chains were introduced to create a "knob," and the heavy chain derived from the 11E6 antibody is mutated such that bulky amino acids were replaced by amino acids with short side chains to create a "hole." In another embodiment, the heavy chain derived from the humanized 11E6 antibody is mutated such that amino acids with large side chains were introduced to create a "knob," and the heavy chain derived from the 1B7 antibody is mutated such that bulky amino acids were replaced by amino acids with short side chains to create a "hole."

In various embodiments, amino acid residues having a larger side chain volume is selected from arginine (R), phenylalanine (F), tyrosine (Y), tryptophan (W). In various embodiments, amino acid residues having a smaller side chain volume is selected from alanine (A), serine (S), threonine (T), valine (V). Accordingly, in exemplary embodiments, to create the "knob," alanine (A), serine (S), threonine (T), valine (V) residues are mutated to arginine (R), phenylalanine (F), tyrosine (Y), tryptophan (W) residues. In exemplary embodiments, to create the "hole", arginine (R), phenylalanine (F), tyrosine (Y), tryptophan (W) residues are mutated to alanine (A), serine (S), threonine (T), valine (V) residues.

In some embodiments, the bispecific antibody of the invention comprises an immunoglobulin heavy chain derived from the humanized 1B7 antibody, which comprises a mutation at T366, numbered according to the EU index as in Kabat. In some embodiments, the mutations are selected from T366R, T366F, T366Y, T366S, or T366W. In an embodiment, the mutation is T366Y. In another embodiment the mutation is T366W. In some embodiments, the bispecific antibody of the invention comprises an immunoglobulin heavy chain derived from the humanized 11E6 antibody, which comprises a mutation at Y407, numbered according to the EU index as in Kabat. In some embodiments, the mutations are selected from Y407A, Y407S, Y407T, and Y407V. In an embodiment, the mutation is Y407T. In another embodiment, the mutation is Y407V. In some embodiments, the mutation is at T366. In an embodiment, the mutation is T366S. In some embodiments, the mutation is at L368. In an embodiment, the mutation is L368A.

In a particular embodiment, the bispecific antibody of the invention comprises an immunoglobulin heavy chain derived from the humanized 1B7 antibody, which comprises a T366W mutations. The bispecific antibody of the invention further includes an immunoglobulin heavy chain derived from the humanized 11E6 antibody, which comprises T366S, L368A, and Y407V mutations.

Other methods for inducing the heterodimerization of the immunoglobulin heavy and/or light chains to form the bispecific antibodies of the invention (e.g., engineering of orthogonal $C_H/C_L$ Fab interfaces) are known in the art and contemplated herein.

In some embodiments, the present bispecific antibodies are stabilized and have extended in vivo half-lives.

In various embodiments, the bispecific antibodies of the invention comprise an IgG constant region. As used herein, the term "constant region" refers to the portion of an immunoglobulin molecule having a more conserved amino acid sequence relative to the other portion of the immunoglobulin, the variable region, which contains the antigen binding site. The constant region contains the CH1, CH2 and CH3 domains of the heavy chain and the CHL domain of the light chain.

In various embodiments, the IgG constant region is derived from the IgG1 subclass of IgGs, but may also be from any other IgG subclasses of given animals. For example, in humans, the IgG class includes IgG1, IgG2, IgG3, and IgG4; and mouse IgG includes IgG1, IgG2a, IgG2b, IgG2c and IgG3. It is known that certain IgG subclasses, for example, mouse IgG2b and IgG2c, have higher clearance rates than, for example, IgG1 (Medesan et al., Eur. J. Immunol., 28:2092-2100, 1998). Thus, when using IgG subclasses other than IgG1, it may be advantageous to substitute one or more of the residues, particularly in the CH2 and CH3 domains, that differ from the IgG1 sequence with those of IgG1, thereby increasing the in vivo half-life of the other types of IgG. In various embodiments, the IgG may be from any animal origin including birds and mammals. In various embodiments, the IgG may be derived from human, rodent (e.g., mouse and rat), donkey, sheep, rabbit, goat, guinea pig, camel, horse, or chicken. In some embodiments, the constant region is derived from human IgG1.

In various embodiments, the bispecific antibodies of the invention comprise an FcRn binding fragment (e.g., Fc or hinge-Fc domain) of an IgG constant region. As used herein, the IgG Fc region refers to the portion of an IgG molecule that correlates to a crystallizable fragment obtained by papain digestion of an IgG molecule. The Fc region includes the C-terminal half of the two heavy chains of an IgG molecule that are linked by disulfide bonds. It has no antigen binding activity but contains the carbohydrate moiety and the binding sites for complement and Fc receptors, including the FcRn receptor. The Fc fragment contains the entire second constant domain CH2 (e.g., residues 231-340 of human IgG1 depicted in FIG. 1, according to the Kabat numbering system) and the third constant domain CH3 (e.g., residues 341-447 of human IgG1 depicted in FIG. 1). The hinge-Fc fragment, as used herein, refers to a region of an IgG molecule including the Fc region (residues 231-447) and a hinge region (residues 216-230 of human IgG1 depicted in FIG. 1) extending from the N-terminus of the Fc region.

The present invention utilizes IgG constant regions that naturally contain an FcRn binding domain. However, in alternative embodiments, constant regions derived from other non-IgG immunoglobulins (e.g., IgE, IgM, IgD, IgA and IgY) or fragments may be utilized. In such embodiments, the non-IgG constant region or fragments thereof may be engineered to contain an FcRn-binding fragment. In such embodiments, the FcRn-binding domain comprises one or more amino acid modifications that increase the affinity of the constant region fragment for FcRn.

In various embodiments, the bispecific antibodies of the invention comprise an IgG constant region that contains one or more amino acid modifications relative to a wild type IgG constant region. In various embodiments, the modifications increase the affinity of the IgG constant region for the FcRn. In some embodiments, the IgG constant region comprises one or more mutations at amino acid residues 251-256, 285-290, 308-314, 385-389 and 428-436, or equivalents thereof. As used herein, all residues of the IgG constant region are numbered according to Kabat et al. (Sequences of Proteins of Immunological Interest, U.S. Department of Health and Human Services, 1991, which is incorporated by reference herein in its entirety) and as presented in FIG. 1 (SEQ ID NO: 21), and include corresponding residues in other IgG constant regions as determined by sequence alignment.

In some embodiments, the bispecific antibodies of the invention comprise an IgG constant region that contains one or more amino acid substitutions at amino acid residue 252, 254, 256, 309, 311, 433 or 434, or equivalents thereof. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the bispecific antibodies of the invention comprise an IgG constant region that contains one or more mutations at amino acid residue 252, 254, 256, 433, 434, or 436. In an embodiment, the IgG constant region includes a triple M252Y/S254T/T256E mutation or YTE mutation. In another embodiment, the IgG constant region includes a triple H433K/N434F/Y436H mutation or KFH mutation. In a further embodiment, the IgG constant region includes an YTE and KFH mutation in combination.

In some embodiments, the bispecific antibodies of the invention comprise an IgG constant region that contains one or more mutations at amino acid residues 250, 253, 307, 310, 380, 428, 433, 434, and 435. Illustrative mutations include T250Q, M428L, T307A, E380A, I253A, H310A, M428L, H433K, N434A, N434F, N434S, and H435A. In an embodiment, the IgG constant region comprises a M428L/N434S mutation or LS mutation. In another embodiment, the IgG constant region comprises a T250Q/M428L mutation or QL mutation. In another embodiment, the IgG constant region comprises an N434A mutation. In another embodiment, the IgG constant region comprises a T307A/E380A/N434A mutation or AAA mutation. In another embodiment, the IgG constant region comprises an I253A/H310A/H435A mutation or IHH mutation. In another embodiment, the IgG constant region comprises a H433K/N434F mutation. In another embodiment, the IgG constant region comprises a M252Y/S254T/T256E and a H433K/N434F mutation in combination.

Additional exemplary mutations in the IgG constant region are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, Ko et al. Nature (2014) 514:642-645, Grevys et al Journal of Immunology. (2015), 194(11):5497-508, and U.S. Pat. No. 7,083,784, the entire contents of which are hereby incorporated by reference.

Amino acid modifications can be made by methods which are well known and routine for the skilled artisan. For example, but not by way of limitation, amino acid substitutions may be accomplished using any well-known PCR-based technique and site-directed mutagenesis (see, for example, Zoller and Smith, *Nucl. Acids Res.* 10:6487-6500, 1982; Kunkel, *Proc. Natl. Acad. Sci USA* 82:488, 1985, which are hereby incorporated by reference in their entireties).

In various embodiments, the one or more mutations in the IgG constant region increases affinity for the neonatal Fc receptor (FcRn). In some embodiments, the one or more mutations in the IgG constant region increases affinity for FcRn at a pH of about 6.0, about 6.1, about 6.2, about 6.3, about 6.4, about 6.5, about 6.6, about 6.7, about 6.8, about 6.9, or about 7.0. In various embodiments, the affinity for FcRn of the bispecific antibodies comprising the modified IgG constant region is increased by about 10%, about 20%, about 30%, about 40%, about 50%, about 60%, about 70%, about 80%, about 90%, about 100%, about 2-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, about 150-fold or about 200-fold, or more, compared to antibodies comprising the wild-type IgG constant region. Affinity for FcRn can be measured by surface plasmon resonance (SPR) measurement using, for example, a BIAcore 2000 (BIAcore Inc.) as described in Popov et al., *Mol. Immunol.,* 33:493-502, 1996 and Karlsson et al., *J. Immunol. Methods,* 145:229-240, 1991, both of which are incorporated by reference in their entireties. In this method, FcRn molecules are coupled to a BIAcore sensor chip (e.g., CM5 chip by Pharmacia) and the binding of modified IgG to the immobilized FcRn is measured at a certain flow rate to obtain sensorgrams using BIA evaluation 2.1 software, based on which on- and off-rates of the modified IgG constant regions, or fragments thereof, to FcRn can be calculated.

In various embodiments, the present bispecific antibodies comprising the modified IgG constant region are stabilized and have extended in vivo half-lives. In various embodiments, the half-lives of the bispecific antibodies comprising the modified IgG constant region is increased by about 10%, about 20%, about 30%, about 40%, about 50%, about 60%, about 70%, about 80%, about 90%, about 100%, about 2-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, about 150-fold or about 200-fold, or more, compared to antibodies comprising the wild-type IgG constant region. The half-life of an antibody comprising modified IgG or fragments thereof can be measured, for example, by pharmacokinetic studies according to the method described by Kim et al. (*Eur. J. Immunol.* 24:542, 1994), which is incorporated by reference herein in its entirety. According to this method, radiolabeled antibodies comprising modified IgG or fragments thereof is injected intravenously into mice and its plasma concentration is periodically measured as a function of time, for example, at 3 minutes to 72 hours after the injection. The clearance curve thus obtained should be biphasic, that is, α-phase and β-phase. For the determination of the in vivo half-life of the antibodies comprising modified IgGs or fragments thereof, the clearance rate in β-phase is calculated and compared with that of antibodies comprising the wild-type IgG.

In various embodiments, the bispecific antibodies of the invention exhibit enhanced in vivo half-life thereby permitting lower effective dosages and/or less frequent dosing of the therapeutic antibodies relative to antibodies comprising wild-type IgG constant regions.

In various embodiments, the bispecific antibodies of the invention exhibit enhanced bioavailability to various tissues or organs relative to antibodies comprising wild-type IgG constant regions. In various embodiments, the bispecific antibodies of the invention exhibit enhanced bioavailability to, without limitation, the lungs, heart, pancreas, liver, kidney, bladder, stomach, large or small intestine, respiratory tract, lymph nodes, nervous tissue (central and/or peripheral nervous tissue), muscle, epidermis, bone, cartilage, joints, blood vessels, bone marrow, prostate, ovary, uterine, tumor or cancer tissue, etc.

In various embodiments, the bispecific antibodies of the invention result in reduced side effects relative to antibodies comprising wild-type IgG constant regions.

The ability of an antibody to bind a specific epitope can be described by the equilibrium dissociation constant ($K_D$). In certain embodiments, the present bispecific antibodies bind the pertussis toxin protein with a $K_D$ of about 20 nM or lower, or about 15 nM or lower, or about 10 nM or lower, or about 5 nM or lower. In an embodiment, the present bispecific antibodies bind the pertussis toxin protein with a $K_D$ of about 5 nM or lower or about 3 nM or lower. In illustrative embodiments, the present bispecific antibodies bind the pertussis toxin protein with a $K_D$ of about 3 nM, about 2.5 nM, about 2 nM, about 1.5 nM, about 1 nM, or about 0.5 nM.

In some embodiments, the present bispecific antibodies described herein compete with an antibody that is capable of binding a pertussis toxin protein. Where the bispecific antibody competes with an antibody (competitor antibody) for binding a pertussis toxin protein, the bispecific antibody of the invention inhibits (completely or partially) binding of the competitor antibody to a measurable extent. The inhibition of binding may be measured by any of the methods known in the art. In general, a bispecific antibody is considered to competitively inhibit binding of a competitor antibody (e.g., mouse 1B7 or 11E6 antibody as described by Sato et al., (1990), Infection and Immunity, 58(10): 3369-3374 or humanized 1B7 antibody as described by Maynard et al., U.S. Pat. No. 8,653,243, which are herein incorporated by reference in their entireties), if binding of the competitor antibody to the antigen is reduced by at least about 10%, at least about 20%, at least about 30%, at least about 40%, at least about 50%, at least about 60%, at least about 70%, at least about 80%, or at least about 90%, in the presence of the bispecific antibody. Thus, in some embodiments, the antibody provided herein binds to a pertussis toxin protein competitively with a mouse 1B7 or 11E6 antibody as described by Sato et al., (1990), Infection and Immunity, 58(10): 3369-3374. In other embodiments, the bispecific antibody provided herein inhibits (completely or partially) the binding of a mouse 1B7 or 11E6 antibody. In some further embodiments, the bispecific antibody provided herein decreases the binding of a mouse 1B7 or 11E6 antibody in a competition assay by about 10%, about 20%, about 30%, about 40%, about 50%, about 60%, about 70%, about 80%, about 90% or about 100%.

Although the embodiments illustrated in the Examples may comprise pairs of variable regions, pairs of full length antibody chains, or pairs of CDR1, CDR2 and CDR3 regions, one from a heavy chain and one from a light chain, a skilled artisan will recognize that alternative embodiments may comprise single heavy chain variable regions or single light chain variable regions, single full length antibody chains, or CDR1, CDR2 and CDR3 regions from one antibody chain, either heavy or light.

Production of Antibodies

Methods for producing antibodies of the invention are described herein. For example, DNA molecules encoding light and/or heavy chains, light chain variable and/or constant regions and/or heavy chain variable and/or constant regions can be chemically synthesized using the sequence information provided herein. Synthetic DNA molecules can be ligated to other appropriate nucleotide sequences, including, e.g., expression control sequences, to produce gene expression constructs encoding the desired antibodies. Alternatively, the sequences provided herein can be cloned out of hybridomas by hybridization techniques or polymerase chain reaction (PCR) techniques using synthetic nucleic acid probes.

Nucleic acids encoding desired antibodies can be incorporated (ligated) into expression vectors, which can be introduced into host cells through transfection, transformation, or transduction techniques. For example, nucleic acids encoding desired antibodies can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, IgG enhancers, and various introns. The gene construct can be introduced into eukaryotic host cells using transfection, transformation, or transduction techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function. In some embodiments, a host cell is transfected with a single vector expressing a polypeptide expressing an entire, or part of, a heavy chain (e.g., a heavy chain variable and/or constant region) or a light chain (e.g., a light chain variable and/or constant region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain or light chain can be produced by growing a host cell transfected with an expression vector encoding such regions, under conditions that permit expression of the polypeptide. Following expression, the polypeptide can be harvested and purified using techniques well known in the art, e.g., affinity tags such as glutathione-S-transferase (GST) and histidine tags or by chromatography (by way of non-limiting example, based on size, charge, and/or specific binding).

A monoclonal antibody that binds the pertussis toxin protein, or an antigen-binding fragment of the antibody, can be produced by growing a host cell transfected, transformed or transduced with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified using techniques well known in the art, e.g., Protein A, Protein G, affinity tags such as glutathione-S-transferase (GST) and histidine tags or by chromatography. It is within ordinary skill in the art to express the heavy chain and the light chain from a single expression vector or from two separate expression vectors.

In various embodiments, the heavy and light chains or fragments thereof derived from the humanized 1B7 antibody and the heavy and light chains or fragments thereof derived the humanized 11E6 antibodies may be induced to heterodimerize to form the bispecific antibodies of the invention via a reduction/oxidation step. In an embodiment, the reduction step utilizes 2-Mercaptoethanolamine (2-MEA).

Antibody Modifications

There are standard methods for reducing or eliminating the antigenicity of antibodies and antibody fragments that are known in the art. When the antibodies are to be administered to a human, the antibodies preferably are "humanized" to reduce or eliminate antigenicity in humans. It is contemplated that the humanized antibodies have at least the same or substantially the same affinity for the antigen as the non-humanized mouse antibody from which it was derived.

However, it is noted that while humanization approaches are known in the art, some humanization approaches are hindered by reductions in affinity (e.g. relative to the original murine antibody). This may be, without wishing to be bound by theory, due to the fact that the CDRs are not maintained workable configuration by the human frameworks. In this case, a small number of changes to the human framework sequences are made. These individual amino acid changes improve the affinity without making significant deviations from the human antibody structure so that the antibodies continue to resemble human antibodies. In that way, the antibodies can be used as for therapeutic purposes in humans without inducing an immune response. The choice of amino acids to change and the specific changes to be made are part of the present invention.

In one humanization approach, chimeric proteins are created in which mouse immunoglobulin constant regions are replaced with human immunoglobulin constant regions. See, e.g., Morrison et al., 1984, Proc. Nat. Acad. Sci. 81:6851-6855, Neuberger et al., 1984, Nature 312:604-608; U.S. Pat. No. 6,893,625 (Robinson); U.S. Pat. No. 5,500,362 (Robinson); and U.S. Pat. No. 4,816,567 (Cabilly). For example, in some embodiments, any one of the variable regions described herein can be paired with a human constant region.

In an approach known as CDR grafting, the CDRs of the light and heavy chain variable regions are grafted into frameworks from another species. For example, murine CDRs and non-CDR residues involved in antigen binding can be grafted into human sequences. Residues involved in maintaining the combining site structure and residues involved in maintaining $V_L$:$V_H$ contact may also be grafted. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) Nature 321: 522-525; Riechmann et al. (1988) Nature 332: 323-327; Verhoeyen et al. (1988) Science 239: 1534-1536; and Winter (1998) FEBS Lett 430: 92-94.

In an approach called grafting of abbreviated CDRs, abbreviated CDRs, as defined by Padlan et al., (1995) Faseb J 9:133-139, and non-CDR residues involved in antigen binding, are transplanted into a human sequence. Residues involved in maintaining the combining site structure and residues involved in maintaining $V_L$:$V_H$ contact may also be grafted.

Other methods to reduce immunogenicity include "SDR-transfer," "veneering," and "Frankensteining." See, e.g., Padlan et al., (1995) FASEB J 9:133-139, Wu et al., (1992) MOL IMMUNOL 29:1141-1146, and Padlan et al., (1991) MOL IMMUNOL 28:489-498. In the SDR-transfer approach, residues involved in antigen binding (i.e., the specificity-determining residues or SDRs) are transplanted into a human sequence. Residues involved in maintaining the combining site structure and residues involved in maintaining $V_L$:$V_H$ contact may also be transplanted. In the veneering approach, the surface accessible amino acid residues in the murine antibody are replaced by amino acid residues more frequently found at the same positions in a human antibody. For example, the framework residues, which are exposed to solvent, are replaced with their homologues from a human sequence. The CDRs and non-CDR residues involved in antigen binding are preserved. In the Frankensteining approach, the CDRs are transplanted into a composite sequence constructed from the most similar human framework regions. Residues involved in maintaining the combining site structure and residues involved in maintaining $V_L$:$V_H$ contact may also be transplanted.

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., NATURE 368:856-859, 1994; Fishwild et al., NATURE BIOTECHNOLOGY 14:845-851, 1996; and Mendez et al., NATURE GENETICS 15:146-156, 1997. Human mAbs can also be prepared and optimized from phage display libraries by techniques referenced in, e.g., Knappik et al., J. MOL. BIOL. 296:57-86, 2000; and Krebs et al., J. Immunol. Meth. 254:67-84 2001).

If the antibody is for use as a therapeutic, it can be conjugated to an effector agent such as a small molecule or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

Methods of Using Antibodies

In one aspect, the method of the invention involves treating a patient with *Bordetella pertussis*, comprising administering to the patient the bispecific antibodies of the invention, or pharmaceutical compositions including the antibody or antibodies.

In another aspect, the method of the invention involves a method of preventing a *Bordetella pertussis* infection, comprising administering to a patient the bispecific antibodies, or pharmaceutical compositions including the antibody or antibodies and, in some embodiments, the patient is at risk for a *Bordetella pertussis* infection (e.g. the patient is a pre-vaccination infant and/or the patient has been exposed to a pertussis toxin).

Leukocytosis or elevation in white blood cell count is characteristic of *Bordetella pertussis* infections. In one embodiment, the method of the invention comprises a reduction in white blood cell count in the patient. In an embodiment, the bispecific antibodies of the invention are similarly effective or even more effective in reducing the white blood cell count of a patient than the use of either of the parent humanized 1B7 or 11E6 antibodies alone or a combination of the two parent antibodies (e.g., administered as a cocktail of two antibodies). In an embodiment, the method of the invention results in an acceleration of the resolution of leukocytosis. In another embodiment, the method of the invention results in a reduction of the maximum white blood cell count during the course of the infection.

In various embodiments, the method of the invention results in an improvement of whooping cough in the patient. In one embodiment, the coughing symptoms of the patient are improved. For example, the method reduces the frequency of coughing or the number of coughs (or coughing episodes) in the patient. In various embodiments, the method reduces the number of coughs or coughing episodes by at least about 1 per hour, at least about 2 per hour, at least about 3 per hour, at least about 4 per hour, at least about 5 per hour, at least about 6 per hour, at least about 7 per hour, at least about 8 per hour, at least about 9 per hour, at least about 10 per hour, at least about 15 per hour, at least about 20 per hour, at least about 25 per hour, at least about 30 per hour, at least about 35 per hour, at least about 40 per hour, at least about 45 per hour, at least about 50 per hour, at least about 55 per hour, at least about 60 per hour, at least about 65 per hour, at least about 70 per hour, at least about 75 per hour, at least about 80 per hour, at least about 85 per hour, at least about 90 per hour, at least about 95 per hour, or at least about 100 per hour. In another example, the method reduces the duration of coughing in the patient. For example, the method reduces the duration of coughing during the course of the infection by at least about three months, about two months, about one month, about 4 weeks, about 3 weeks, about 2 weeks, about 1 week, about 5 days, about 4 days, about 3 days, about 2 days, or about 1 day. In a further embodiment, the number of whoops is reduced in the patient. In an embodiment, the bispecific antibodies of the invention are similarly effective or even more effective in improving whooping cough than the use of either of the parent humanized 1B7 or 11E6 antibodies alone or a combination of the two parent antibodies (e.g., administered as a cocktail of two antibodies).

In another embodiment, the method of the invention reduces the level of the *Bordetella pertussis* bacteria in the nasopharynx of the patient. In a further embodiment, the method of the invention reduces the level of the *Bordetella pertussis* bacteria in the lung of the patient (e.g. bacterial lung colonization). For example, the method reduces the *Bordetella pertussis* levels in the nasopharynx and/or the lungs by about 95%, about 90%, about 80%, about 70%, about 60%, about 50%, about 40%, about 30%, about 20%, about 10%, or about 5%. In an embodiment, the bispecific antibodies of the invention are similarly effective or even more effective in reducing the levels of the *Bordetella pertussis* bacteria in the nasopharynx and/or the lungs of the patient than the use of either of the parent humanized 1B7 or 11E6 antibodies alone or a combination of the two parent antibodies (e.g., administered as a cocktail of two antibodies).

In one embodiment, the method of the invention may be utilized to result in neutralization (inhibition or antagonization) of the pertussis toxin protein. For example, antibodies of the invention can bind to the pertussis toxin protein so as to partially or completely inhibit one or more biological activities of the pertussis toxin protein. Among the biological activities of a pertussis toxin protein that a neutralizing antibody may inhibit or block is the ability of a pertussis toxin protein to bind cellular receptors. The receptor binding region of a pertussis toxin protein consists of four polypeptide subunits referred to as subunit S2, subunit S3, subunit S4 and subunit S5, respectively. Examples of cellular receptors that are bound by the subunits S2, S3, S4, and 85 of a pertussis toxin protein are members of the N-linked sialoglycoprotein family such as fetuin, haptoblobin, and transferrin. In an illustrative embodiment, the bispecific antibodies of the invention prevent the pertussis toxin protein from binding to its cellular receptor. In another embodiment, the bispecific antibodies of the invention alter the intracelluar trafficking steps of the pertussis toxin such that the toxin does not reach the cellular cytosol. Another important activity of a pertussis toxin protein that may be inhibited by antibodies of the invention is the enzymatic activity of the pertussis toxin protein as ADP ribosylase towards G proteins. The subunit conferring to the enzymatic activity as ADP-ribosylase in a pertussis toxin protein is subunit S1. In some embodiments, the pertussis toxin protein is a pertussis holotoxin. A pertussis holotoxin as referred to herein as a pertussis toxin protein that includes all five pertussis toxin protein subunits. In other embodiments, the pertussis toxin protein is a truncated pertussis toxin protein. A truncated pertussis protein as referred to herein includes at least one of the pertussis toxin protein subunits (i.e., S1, S2, S3, S4 and S5). Pertussis toxin proteins of various forms are described in, for example, U.S. Pat. No. 8,653,243, which is herein incorporated by reference in its entirety. In an embodiment, the bispecific antibodies of the invention are similarly effective or even more effective in neutralizing the pertussis toxin protein than the use of either of the parent humanized 1B7 or 11E6 antibodies alone or a combination of the two parent antibodies (e.g., administered as a cocktail of two antibodies).

In various embodiments, the present compositions and methods are useful in the treatment or prevention of any of the stages of pertussis infections. For example, the incubation period of pertussis is commonly 7-10 days, with a range of 4-21 days, and rarely may be as long as 42 days. In various embodiments, the present compositions and methods increase the length of the incubation period by making the infection more difficult to come about. The clinical course of the illness is divided into three stages. The first stage, the catarrhal stage, is characterized by the insidious onset of coryza, sneezing, low-grade fever, and a mild, occasional cough, similar to the common cold. The cough gradually becomes more severe, and after 1-2 weeks, the second, or paroxysmal stage, begins. In various embodiments, the present compositions and methods, reduce the length of the catarrhal stage and, optionally, prevent it from advancing to the paroxysmal stage. In various embodiments, the present compositions and methods treat one or more of coryza, sneezing, low-grade fever, and cough. It is during the paroxysmal stage that the diagnosis of pertussis is usually suspected. Characteristically, a patient has bursts, or paroxysms, of numerous, rapid coughs, apparently due to difficulty expelling thick mucus from the tracheobronchial tree. At the end of the paroxysm, a long inspiratory effort is usually accompanied by a characteristic high-pitched whoop. During such an attack, the patient may become cyanotic. Children and young infants, especially, appear very ill and distressed. Vomiting and exhaustion commonly follow the episode. In various embodiments, the present compositions and methods reduce the quantity and/or frequency of paroxysms. In various embodiments, the present compositions and methods prevent a patient from becoming cyanotic. Paroxysmal attacks occur more frequently at night, with an average of 15 attacks per 24 hours. During the first 1 or 2 weeks of this stage, the attacks increase in frequency, remain at the same level for 2 to 3 weeks, and then gradually decrease. The paroxysmal stage usually lasts 1 to 6 weeks but may persist for up to 10 weeks. In various embodiments, the present compositions and methods reduce the length of this stage. In the convalescent stage, recovery is gradual. The cough becomes less paroxysmal and disappears in 2 to 3 weeks. In various embodiments, the present compositions and methods accelerate the onset of this stage and/or reduce its duration. Further, in various embodiments, the present compositions and methods prevent or reduce the recurrence of paroxysms, which may occur with subsequent respiratory infections. In various embodiments, the present compositions and methods prevent or reduce one or more of the onset of secondary bacterial pneumonia, neurologic complications such as seizures and encephalopathy, hypoxia, otitis media, dehydration, pneumothorax, epistaxis, subdural hematomas, hernias, rectal prolapsed, difficulty sleeping, urinary incontinence, pneumonia, and rib fracture. Further, in some embodiments, the present compositions and methods reduce or prevent necrotizing bronchiolitis, pneumonia (e.g. from *Bordetella pertussis*), pulmonary edema, pulmonary hypertension, and death. In an embodiment, the bispecific antibodies of the invention are similarly effective or even more effective in preventing or treating any of the stages of pertussis infections or any of the symptoms of pertussis infections than the use of either of the parent humanized 1B7 or 11E6 antibodies alone or a combination of the two parent antibodies (e.g., administered as a cocktail of two antibodies).

In some embodiments, the bispecific antibodies of the present invention have a peak in a serum concentration (e.g. a beta half-life) of at least about 30, or about 35, or about 40, or about 45, or about 50, or about 55, or about 60, or about 65, or about 70, or about 75, or about 80 hours post-administration or at least about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, or about 25 days).

In some embodiments, the bispecific antibodies of the present invention have prolonged half-lives. In some embodiments, the antibodies of the present invention have an in vivo half-life of about 200, or about 225, or about 250, or about 275, or about 300 hours or about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, or about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, or about 50 days, e.g. about 1 or about 2 weeks, or about 3 weeks, about 4 weeks, about 5 weeks, about 6 weeks, about 7 weeks, or about 8 weeks). In an embodiment, the bispecific antibodies of the present invention have in vivo half-life of about 20 days to about 40 days.

Accordingly, in some embodiments, a patient may receive a first administration (e.g. infusion or intramuscular (IM) injection) of the inventive antibodies as part of a treatment method and may receive a further administration (e.g. infusion or intramuscular injection) after a peak in serum concentration and/or the in vivo half-life of the present bispecific antibodies (e.g. the dose of the further administration may be identical to the first administration or may be lower, e.g. a maintenance dose). In some embodiments, the further administration is about one day from the first administration, or about one week from the first administration. In some embodiments, the present methods provide for about 1-3 (e.g. about 1, or about 2, or about 3) doses (e.g. IV doses or IM doses) of the antibodies of the present invention per week (or about every 5, or 6, or 7, or 10 days). In some embodiments, the present methods maintain a therapeutic window of antibody levels in the blood serum of about 5 μg/mL, about 10 μg/mL, about 20 μg/mL, about 25 μg/mL, about 50 μg/mL, about 75 μg/mL, or about 100 μg/mL, or about 125 μg/mL, or about 150 μg/mL, or about 175 μg/mL, or about 200 μg/mL, or about 225 μg/mL, or about 250 μg/mL, or about 300 μg/mL. In some embodiments, the present methods allow for infrequent dosing and/or lower dosing (e.g. longer half-lives permitting lower and less frequent dosing).

In another embodiment, the method includes administering to a patient the bispecific antibody of the invention, along with antimicrobial agents. It is contemplated that co-administration of the present bispecific antibody along with antimicrobial agents produces synergistic effects. Illustrative antimicrobial agents that may be used for the invention include, but are not limited to azithromycin, clarithromycin, erythromycin, trimethoprim-sulfamethoxasole, roxithromycin, ketolides (e.g., telithromycin) ampicillin, amoxicillin, tetracycline, chloramphenicol, fluoroquinolones (e.g., ciprofloxacin, levofloxacin, ofloxacin, moxifloxacin), and cephalosporins. In an embodiment, the antimicrobial agent is erythromycin.

In various embodiments, the method of the invention treats human patients. In an embodiment, the human patient is an infant. In an embodiment, the human patient is a newborn. In another embodiment, the human patient is a neonate who is less than four weeks old, less than three weeks old, less than two weeks old, less than one week old, less than six days old, less than five days old, less than four days old, less than three days old, less than two days old, or less than one day old. In some embodiments, the human is one month old, two months old, three months old, four months old, five months old, or six months old. In some embodiments, the human has an age in a range of from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In a further aspect, the method of the invention prevents *Bordetella pertussis* infection in a subject previously exposed to the bacteria, comprising administering to the subject the bispecific antibody of the invention, or pharmaceutical compositions including the antibody or antibodies. In various embodiments, the method provides an effective prophylactic treatment in preventing *Bordetella pertussis* infection in a subject exposed to the bacteria.

In various embodiments, the bispecific antibodies of the invention exhibit extended half-life, and based on the exponential nature of half-life, small changes to the length of half-life can cause substantial improvements to the duration of prophylaxis. Accordingly, in various embodiments, the bispecific antibodies of the invention provide a prophylaxis time (i.e., the time that the subject is protected from *Bordetella pertussis* infection) of at least one day, at least two days, at least three days, at least four days, at least five days, at least six days, at least 1 week, at least 2 weeks, at least 3 weeks, at least 4 weeks, at least 1 month, at least 2 months, at least 3 months, at least 4 months, at least 5 months, at least 6 months, or at least 1 year.

In some embodiments, the bispecific antibody of the invention is utilized in prophylactic applications in a subject who has not been previously vaccinated against the bacteria. In an embodiment, the antibody of the invention is administered to a subject as a prophylactic treatment prior to the subject receiving a pertussis vaccination. In various embodiments, the antibody of the invention is utilized in prophylactic treatments of a subject who is less than one year old, less than eleven months old, less than ten months old, less than nine months old, less than eight months old, less than seven months old, less than six months old, less than five months old, less than four months old, less than three months old, less than two months old, less than one month old, less than four weeks old, less than three weeks old, less than two weeks old, less than one week old, less than six days old, less than five days old, less than four days old, less than three days old, less than two days old, or less than one day old. Accordingly, in some embodiments, the present methods involving bridging the time between birth and vaccination in an infant patient.

In various embodiments, the methods of the invention treat or prevent *Bordetella pertussis* infection in a subject previously vaccinated against the bacteria. In an embodiment, the subject is an infant or child vaccinated with DtaP (e.g., INFANRIX (with three antigens, mostly pertussis toxin (PT) and FHA), TRIPEDIA (which contains two components, FHA and PT, in equal amounts) and DAPTACEL (which contains five components, PT, FHA, pertactin, and fimbriae types 2 and 3)). In another embodiment, the subject is an adult vaccinated with the pertussis booster vaccine Tdap (e.g. BOOSTRIX (with three pertussis antigens (PT, FHA, and pertactin) in a reduced quantity compared with INFANRIX) and ADACEL (with the same five pertussis components as DAPTACEL but with a reduced quantity of PT). In other embodiments, the patient of the present invention may or may not have received any one of the following pertussis combination vaccines: PEDIARIX, PENTACEL, or KINRIX.

It is contemplated that the bispecific antibodies of the invention may further function as adjuvant for vaccinations such as DtaP or Tdap. Further, in various embodiments, the methods of the invention treat or prevent *Bordetella pertussis* infection in a subject that has not been previously vaccinated against the bacteria In various embodiments, the present compositions and methods supplement or supplant treatment with palivizumab (SYNAGIS).

In various embodiments, the present compositions and methods can treat pertussis infections that have various strains as their etiology, including, by way of non-limiting example, pertactin-negative pertussis.

Furthermore, *Bordetella parapertussis* is a closely related species *Bordetella pertussis*. Both bacteria are linked to outbreaks of whooping cough in humans and produce similar virulence factors. Co-infection of *Bordetella pertussis* and *Bordetella parapertussis* is not unusual. Accordingly, in one aspect of the invention, the method of the invention involves treating a patient with *Bordetella parapertussis*, comprising administering to the patient the present bispecific antibody, or pharmaceutical compositions including the antibody or antibodies. In another aspect of the invention, the method of the invention prevents *Bordetella parapertussis* infection in a subject previously exposed to the bacteria, comprising administering to the subject the present bispecific antibody, or pharmaceutical compositions including the antibody or antibodies.

In various embodiments, the methods of the invention are effective in treating *Bordetella pertussis* infection and/or *Bordetella parapertussis* infection when the bispecific antibody is administered to the patient at about 3 months after infection. In other embodiments, the methods of the invention are effective in treating *Bordetella pertussis* infection and/or *Bordetella parapertussis* infection when the bispecific antibody is administered to the patient at about 2 months, about 1 month, about 4 weeks, about 3 weeks, about 2 weeks, about 7 days, about 6 days, about 5 days, about 4 days, about 3 days, about 2 days, or about 1 day after infection. In an embodiment, the bispecific antibody is administered to the patient on the day of infection.

As used herein, "treat," "treating" and "treatment" mean the treatment of a disease in a mammal, e.g., in a human. In various embodiments, this includes: (a) inhibiting the disease, i.e., arresting its development and/or (b) relieving the disease, i.e., causing regression of the disease state.

Pharmaceutical Compositions and Administration

The pharmaceutical compositions of the invention can be administered for therapeutic or prophylactic treatment. For such uses, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies, such as those disclosed herein, can be presented in a dosage unit form and can be prepared by any suitable method. A pharmaceutical composition should be formulated to be compatible with its intended route of administration. Examples of routes of administration are oral, intranasal, pulmonary, intravenous (IV), intradermal, inhalation, transdermal, topical, transmucosal, subcutaneous, intramuscular (IM), intraperitoneal, and rectal administration. In an embodiment, the route of administration for antibodies of the invention is IV infusion. In another embodiment, the route of administration for antibodies of the invention is IM injection.

Useful formulations can be prepared by methods well known in the pharmaceutical art. For example, pharmaceutical compositions of the invention can be formulated as a colloidal dispersion system, macromolecular complex, nanocapsule, microsphere, bead, oil-in-water emulsion, micelle, mixed micelle, or liposome. For example, see *Remington's Pharmaceutical Sciences,* 18th ed. (Mack Publishing Company, 1990).

Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, CREMOPHOR EL® polyethoxylated castor oil (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can also contain other compatible therapeutic agents. For example, the composition may additionally include antimicrobial agents described herein.

The combined administrations contemplates co-administration, using separate formulations or a single pharmaceutical formulation, and consecutive administration in either order, wherein preferably there is a time period while both (or all) active agents simultaneously exert their biological activities.

It will be appreciated that the actual dose of the antibodies to be administered according to the present invention will vary according to, for example, the particular dosage form and the mode of administration. Many factors that may modify the action of the antibodies (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the bispecific antibody can be administered in unit dosage forms containing, for example, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween.

In one embodiment, the bispecific antibody is administered at an amount of from about 0.01 mg to about 100 mg daily, an amount of from about 0.01 mg to about 1,000 mg daily from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the antibody is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween.

In some embodiments, a suitable dosage of the bispecific antibody is in a range of about 0.01 mg/kg to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, or about 100 mg/kg body weight, inclusive of all values and ranges therebetween. In other embodiments, a suitable dosage of the antibody in a range of about 0.01 mg/kg to about 100 mg/kg of body weight, in a range of about 1 mg/kg to about 100 mg/kg of body weight, in a range of about 1 mg/kg to about 90 mg/kg of body weight, in a range of about 1 mg/kg to about 80 mg/kg of body weight, in a range of about 1 mg/kg to about 70 mg/kg of body weight, in a range of 1 mg/kg to about 60 mg/kg of body weight, in a range of 1 mg/kg to about 50 mg/kg of body weight, in a range of 1 mg/kg to about 40 mg/kg of body weight, in a range of 1 mg/kg to about 30 mg/kg of body weight, in a range of 1 mg/kg to about 20 mg/kg of body weight, in a range of about 5 mg/kg to about 50 mg/kg of body weight, in a range of about 5 mg/kg to about 40 mg/kg of body weight, in a range of about 5 mg/kg to about 30 mg/kg of body weight, in a range of about 5 mg/kg to about 20 mg/kg of body weight, inclusive of all values and ranges therebetween.

In accordance with certain embodiments of the invention, the bispecific antibody may be administered, for example, more than once daily, about once per day, about every other day, about every third day, about once a week, about once every two weeks, about once every month, about once every two months, about once every three months, about once every six months, or about once every year.

Antibody can be administered on multiple occasions. Intervals between single dosages can be weekly, monthly or yearly. Intervals can also be irregular as indicated by measuring blood levels of the antibody in the subject. In some embodiments, the antibody can be administered as a sustained release formulation, in which case less frequent administration is required.

In some methods, the bispecific antibody of the invention is administered at a dosage to achieve a plasma or serum antibody concentration of 1-1000 μg/ml and in some methods 25-300 μg/ml. For example, the antibody of the invention can be administered at a dosage to achieve a plasma or serum level of about 1-1000 μg/ml, 1-900 μg/ml, 1-800 μg/ml, 1-700 μg/ml, 1-600 μg/ml, 1-500 μg/ml, 1-400 μg/ml, 1-300 μg/ml, 1-200 μg/ml, 1-100 μg/ml, 10-500 μg/ml, 10-400 μg/ml, 10-300 μg/ml, 10-200 μg/ml, 10-100 μg/ml, 100-400 μg/ml, 100-300 μg/ml, or 100-200 μg/ml, inclusive of all values and ranges therebetween. For example, the antibody of the invention can be administered at a dosage to achieve a plasma or serum level of about 1 μg/ml, about 5 μg/ml, about 10 μg/ml, about 15 μg/ml, about 20 μg/ml, about 25 μg/m, about 30 μg/ml, about 35 μg/ml, about 40 μg/ml, about 45 μg/ml, about 50 μg/ml, about 55 μg/ml, about 60 μg/ml, about 65 μg/ml, about 70 μg/ml, about 75 μg/ml, about 80 μg/ml, about 85 μg/ml, about 90 μg/ml, about 95 μg/ml, about 100 μg/ml, about 105 μg/ml, about 110 μg/ml, about 115 μg/ml, about 120 mg μg/ml, about 125 μg/ml, about 130 μg/ml, about 135 μg/ml, about 140 μg/ml, about 145 μg/ml, about 150 μg/ml, about 155 μg/ml, about 160 μg/ml, about 165 μg/ml, about 170 μg/m, about 175 μg/ml, about 180 μg/ml, about 185 μg/ml, about 190 μg/ml, about 195 μg/ml, about 200 μg/ml, about 205 μg/ml, about 210 μg/ml, about 215 μg/ml, about 220 mg μg/ml, about 225 μg/ml, about 230 μg/ml, about 235 μg/ml, about 240 μg/ml, about 245 μg/ml, about 250 μg/ml, about 255 μg/ml, about 260 μg/ml, about 265 μg/ml, about 270 μg/ml, about 275 μg/ml, about 280 μg/ml, about 285 μg/ml, about 290 μg/ml, about 295 μg/ml, or about 300 μg/ml.

In some methods, the bispecific antibody of the invention achieves a potency of at least about 1 EU/ug, at least about 2 EU/ug, at least about 3 EU/ug, at least about 4 EU/ug, at least about 5 EU/ug, at least about 6 EU/ug, at least about 7 EU/ug, at least about 8 EU/ug, at least about 9 EU/ug, at least about 10 EU/ug, at least about 15 EU/ug, at least about 20 EU/ug, at least about 25 EU/ug, at least about 30 EU/ug, at least about 35 EU/ug, at least about 40 EU/ug, at least about 45 EU/ug, at least about 50 EU/ug, at least about 55 EU/ug, at least about 60 EU/ug, at least about 65 EU/ug, at least about 70 EU/ug, at least about 75 EU/ug, at least about 80 EU/ug, at least about 85 EU/ug, at least about 90 EU/ug, at least about 95 EU/ug, at least or about 100 EU/ug. In some methods, the bispecific antibody of the invention achieves a potency of at least about 1 EU/ml, at least about 2 EU/ml, at least about 3 EU/ml, at least about 4 EU/ml, at least about 5 EU/ml, at least about 6 EU/ml, at least about 7 EU/ml, at least about 8 EU/ml, at least about 9 EU/ml, at least about 10 EU/ml, at least about 15 EU/ml, at least about 20 EU/m, at least about 25 EU/ml, at least about 30 EU/ml, at least about 35 EU/ml, at least about 40 EU/ml, at least about 45 EU/ml, at least about 50 EU/ml, at least about 55 EU/ml, at least about 60 EU/ml, at least about 65 EU/ml, at least about 70 EU/ml, at least about 75 EU/ml, at least about 80 EU/ml, at least about 85 EU/ml, at least about 90 EU/ml, at least about 95 EU/ml, at least or about 100 EU/ml. EU stands for equivalent units as defined by the WHO polyclonal serum standard. In various embodiments, the antibody of the invention is able to maintain potency after at least about 1 day, about 2 days, about 3 days, about 4 days, about 5 days, about 6 days, about 1 week, about 2 weeks, about 3 weeks, about 4 weeks, about 5 months, about 6 months, about 7 months, about 8 months, about 9 months, about 10 months, about 11 months, or about 12 months.

Dosage and frequency vary depending on factors such as route of administration, dosage amount, the disease being treated, and the half-life of the antibody in the patient. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime. Illustrative dosing frequencies are once per day, twice per day, three times per day, once per week and once every two weeks. In some embodiments, dosing is once every two weeks.

The invention also provides kits that can simplify the administration of any agent described herein (e.g. the humanized antibodies with or without various combination agents). An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

In some embodiments, the kit may comprises a pre-filled syringe in unit dose form (e.g. an injector pen). In various embodiments, the kits are suited for use away from a traditional medical center, e.g. in the field, e.g. in the third world.

EXAMPLES

Example 1. Characterization of the Parental Humanized 1B7 and 11E6 Antibodies Methodology Large-scale preparations of hu1B7 and hu1E6 were commercially performed using polyclonal CHO cell lines followed by protein A chromatography, anion chromatography and buffer exchange into PBS pH 7.0. Fab fragments were prepared by digestion of the parent monoclonals using immobilized papain (Thermo Scientific Pierce), then purified by protein A chromatography and stored in PBS pH 7.4.

The PT holotoxin (PT) and its B subunit (PT-B) were obtained from List Biological Laboratories. The A subunit (PT-220K), a version of the pertussis toxin A subunit truncated at residue 220 and appended with a terminal lysine residue and hexa-histidine tag was expressed from plasmid pAK400. Briefly, BL21(DE3) cells containing the expression vector were grown in TB at 25° C. to an OD of 1.5, then induced with 1 mM IPTG for 5 hours. Cell pellets were collected and the periplasmic contents recovered by osmotic shock. PT-220K was purified by immobilized metal affinity chromatography, followed by size exclusion chromatography (S75, AKTA FPLC). PT-220K was biotinylated via its sole lysine using the EZ-Link Sulfo-NHS-Biotin reagent (Thermo Scientific) by incubation at 4° C. overnight with a 50-fold excess of biotin followed by buffer exchange into PBS pH 7.4. Biotinylation was confirmed with ELISA, in which a hu1B7 coat was used to capture PT-220K which was then detected with streptavidin-HRP (BD Pharmingen).

The hu11E6 antibody sequence was submitted to a public Rosetta antibody server for modeling. Four models with diverse structures were selected and submitted to PatchDock for an initial docking estimate, using the residues within 10 angstroms of the sugar residues on PT structure 1PTO26 as a constraint for binding area. The best docking run for each antibody structure was submitted to Rosetta Docking for refinement. The epitope for the top docking runs was defined as all residues on the PT structure within 4 Å of the CDRs. The final consensus epitope is defined as residues consistently contacted in both the S2 and S3 subunits. An average plane was calculated from the coordinates of all surface exposed residues in each epitope, and a line normal to this plane was added to the final graphic using a custom PyMol script.

All ELISAs followed the same general procedure, with specific modifications detailed below.

First, a high-binding 96-well ELISA plate (Costar) was incubated overnight at 4° C. with the coat protein in PBS, pH 7.4. Second, the plate was blocked. Third, protein dilutions were prepared in the plate in duplicate. After any additional protein incubation steps, the secondary antibody was added to the plate. After the final incubation and washes, the plate was developed with TMB substrate (Thermo Fisher Scientific), quenched with 1N HCl and the absorbance measured at 450 nm using a SpectraMax M5. All incubation steps proceeded for one hour at room temperature, wash steps in between incubation steps used PBS with 0.05% tween-20 (PBST); while the blocking buffer and assay diluent used was PBS with 5% powdered milk (PBSTM). Experiments were performed in triplicate.

For the PT sandwich ELISA, the plate was coated with 1 ug/mL of murine 1B7 or 11E6, blocked, then incubated with 70-100 nM of PT-220K, PT-B, or full PT. The sandwich was completed with 1 ug/mL human 1B7 or 11E6, labeled with a 1:2500 dilution of goat-anti-human Fc-HRP (Thermo Scientific Pierce), and developed as above.

For the PT binding ELISA, the plate was coated with 0.2 ug/mL PT, blocked, then incubated with antibody dilutions starting from 5 ug/mL (hu1B7 variants) or 10 ug/mL (hu11E6 variants). Binding was detected using goat-anti-human constant kappa-HRP antibody (Thermo Scientific Pierce) at a 1:1250 dilution and signal developed and measured as described above.

For the bispecific sandwich ELISA, the plate was coated with 1 ug/mL PT-B, blocked, then incubated with antibody dilutions starting from 20 ug/mL. Following incubation with 1 ug/mL PT-220K-biotin, binding was detected with streptavidin-HRP (BD Pharmingen) at a 1:5000 dilution and signal developed and measured as described above.

PT binding affinity was determined by competition ELISA. A high-binding plate was coated with 0.2 ug/mL PT and blocked as described above. While the plate was blocking, 3 nM (mAbs and bispecific) or 6 nM (Fabs) of each protein was incubated with dilutions of PT starting from 200 nM. After equilibration for an hour at room temperature, the PT/antibody mixtures were transferred to the washed ELISA plate in duplicate and allowed to incubate for 15 minutes at room temperature to capture unbound antibody. Binding was detected with goat-anti-human Fc-HRP (monoclonal and bispecific antibodies) or goat-anti-human constant kappa-HRP (Fabs fragments) and signal developed as above. The resulting curves were fit to equilibrium binding equations corrected for bivalent binding where appropriate. Experiments were performed in triplicate.

Results

Pertussis toxin (PT) is an AB5 toxin, with the S1 subunit comprising the "active" A subunit and subunits S2 through S5 comprising the receptor "binding" B subunit. The epitope for the humanized 1B7 antibody (hu1B7) is primarily localized to the S1 subunit, and was finely resolved using a combined yeast display and high-throughput sequencing technique. Although detailed epitope mapping of the humanized 11E6 antibody (hu11E6) has not been performed, the antibody is known to bind similar epitopes present in the homologous S2 and S3 subunits and appears to interfere with toxin binding to glycosylated and sialylated cellular receptors. Without wishing to be bound by theory, it is believed that the combined use of hu1B7 and hu11E6 may result in synergy due to a more complete neutralization of the toxin when the binding and catalytic activities of the toxin are blocked. This effect would be maximal if the 1B7 and 11E6 epitopes on a single toxin molecule could be simultaneously bound by their respective antibodies. To evaluate this as a possible mechanism, experiments were carried out to confirm binding of one hu1B7 or hu11E6 antibody did not preclude binding of a second antibody to the same toxin molecule.

A series of ELISA assays were performed in which one antibody (murine 1B7 or 11E6) was used to capture PT, which was then detected by a second antibody (hu1B7 or hu11E6; FIG. 2A). As expected from the stoichiometry of the epitopes, the full-length toxin can be sandwiched between m1B7 and hu11E6 or m11E6 and hu11E6, while the B subunit alone can be sandwiched by m11E6 and hu11E6. This result confirmed that hu1B7 and hu11E6 can simultaneously bind the same toxin molecule, and suggested multiple bispecific antibodies would also be able to bind a single toxin molecule to block several epitopes. These results also suggested that synergy could be achieved when multiple antibodies or a bispecific antibody bind the toxin molecule.

To further understand the possible antibody-PT binding configurations, the unique epitopes recognized by hu1B7 and hu11E6 were mapped onto the crystal structure of pertussis toxin (FIG. 2B). The hu1B7 epitope has been previously resolved experimentally, but the precise hu11E6 epitopes are unknown. The general binding area of hu11E6 was identified by docking Rosetta models of the antibody onto the toxin, guided by the location of oligosaccharides in a relevant crystal structure (PDB ID 1PTO). The resulting structure showed that the two hu11E6 epitopes and single hu1B7 epitope were located on different faces of PT and were oriented in opposing directions. The midpoints of any two epitopes were approximately 50 Å apart, which was much narrower than the typical distance for one antibody crosslinking two epitopes of ~130 Å. A line normal to the best-fit plane calculated from the solvent-exposed residues was used to approximate the orientation of an antibody bound to the PT surface. Even considering a large elbow angle of 125° between the variable and constant regions, the geometry suggested that a single antibody molecule, whether monoclonal or bispecific, would only be able to interact with a single epitope at a time. These data suggested that complete blockade of these PT epitopes would thus require a stoichiometry of three antibodies for every PT molecule.

Example 2. Expression and Purification of a Stable hu1B7/hu11E6 Bispecific Antibody Methodology Bispecific constructs were generated by introducing the T366Y (knob, hu1B7H+) or Y407T (hole, hu11E6H−) point mutations into an antibody expression vector containing human constant heavy regions. The modified heavy chain and native light chain vectors were transfected in a 1:1 ratio into confluent T-150 flasks containing adherent CHO-K1 cells using Lipofectamine 2000 (Life Technologies), Supernatant was collected over one week, purified using protein A chromatography and stored in PBS pH 7.4. Bispecific antibody was prepared by incubating a 1:1 molar ratio of the hu1B7H+ and hu11E6− parental antibodies at 1 mg/mL in PBS pH 7.4 with 10 mM EDTA and 50 mM 2-MEA (Thermo Scientific Pierce) for 90 minutes at 37° C. The partially reduced sample was then buffer exchanged into PBS pH 7.4 and 480 stored overnight at 4° C. to allow re-oxidation and heterodimerization.

Results

A bispecific antibody with natural architecture was constructed using the knobs and holes platform with a controlled reducing step (FIG. 3A). The resulting human IgG1 bispecific was structurally similar to the hu1B7 and hu11E6 monoclonal antibodies, with the added benefits of low immunogenicity and enhanced circulating half-life due to FcRn binding.

To make the bispecific antibody, the T366Y "knob" mutation was introduced into the CH3 domain of hu1B7 to generate chain hu1B7H+, while the Y407T "hole" mutation was introduced into the CH3 domain of hu11E6 to generate chain hu11E6H−. These two parent antibodies were transiently expressed in separate CHO cell cultures and purified via protein A chromatography. The parents were combined in an equimolar ratio and subjected to a controlled reducing step using 2-Mercaptoethanolamine (2-MEA) to generate the heterodimeric bispecific antibody (FIG. 3B). Both parent protein preparations showed the presence of half-antibody at ~75 kDa, due to the destabilizing effect of the knob and hole mutations in the homodimers. SDS-PAGE analysis of the bispecific product after reduction with 2-MEA and re-oxidation showed significantly less of the half antibody and high molecular weight species.

The hu1B7H+, hu11E6H− and hu1B7/hu11E6 bispecific antibodies were digested with IdeS protease to form F(ab')2 to reduce the molecular weight while retaining pairing information. LC/MS of the F(ab')2 was run on a binary mixture of the parent antibodies as well as the bispecific (FIG. 3C). The hu1B7H+ and hu11E6H− parent antibodies had intact masses of ~96.7 and 99.1 kDa respectively, with slight differences in peak intensity due to differences in ionization efficiency. The hu1B7/hu11E6 bispecific antibody had a major peak at ~97.9 kDa, which was the expected molecular weight based on amino acid sequence. A small peak was likely part of the major peak while the bispecific peak at ~98.2 kDa may indicate some light chain rearrangement during the 2-MEA reduction step. However, this was not previously shown to be an issue using the same reagent at a higher concentration for an extended period of time.

Example 3. Biophysical Characterization of Bispecific Antibodies

Methodology

For mass spectrometry, 100 μg each of the hu1B7-hu11E6 bispecific antibody and the knob and hole parent antibodies was digested with the IdeS enzyme (Promega) for 1 hour at 37° C. The digested product was run on a SUPERDEX™ S200 size exclusion column (Akta, GE Healthcare) with PBS pH 7.4 as a running buffer. The 100 kDa peak (based on MW standards) was collected and buffer exchanged into 50 mM Ammonium Acetate using a centrifugal filter (Amicon). The digested antibodies were analyzed by LC-MS on an Orbitrap Fusion mass spectrometer (ThermoFisher). A linear gradient of 0.1% formic acid and water and 0.1% formic acid and acetonitrile over 7 minutes was used to elute the digested antibodies from a protein microtrap (Optimize Technologies). The Orbitrap Fusion was operated in Intact Protein Mode at 60000 resolution from 1800-3000 m/z, with 5 microscans and a source fragmentation energy of 35V. Following acquisition, data was deconvoluted using MagTran and Protein Deconvolution Software 4.0.

To assess protein size and purity, 3 μg of each purified protein was analyzed by SDS-PAGE. Proteins were incubated with reducing or non-reducing loading buffer and incubated for 5 minutes at 80° C. or 30 s at 42° C. respectively. The protein was loaded onto a 10% acrylamide gel and run at 120V to completion prior to staining with GelCode Blue (ThermoFisher).

To assess protein stability, the antibody thermal melting temperature was measured with a protein thermal shift assay. Purified antibodies were prepared at 400, 200, and 100 ug/mL in triplicate and mixed with protein thermal shift dye (Life Technologies) as described in the product literature. Quantification of fluorescence was measured using a ViiA-7 instrument at a ramp rate of 1° C./minute, with derivative Tm values calculated from Protein Thermal Shift software (Applied Biosystems, V1.2).

Results

Monoclonal hu1B7 and hu11E6 and their Fab fragments were produced as controls. The monoclonal antibodies were expressed in transient CHO cell cultures and purified by protein A and anion exchange chromatography. The Fab fragments were generated by subsequent digestion of purified antibody with immobilized papain, followed by protein A chromatography to remove undigested antibody and free Fc domains. Reducing and non-reducing SDS-PAGE analysis determined that the proteins were pure (~90% or higher) and of the expected size (FIG. 4A). Reducing lanes showed characteristic bands at ~50 kDa (intact immunoglobulin heavy chain) and ~25 kDa (light chain and Fab heavy chain), while non-reducing lanes showed single bands at ~150 kDa (intact immunoglobulin and bispecific antibody) and ~50 kDa (Fabs).

Figure 4B:
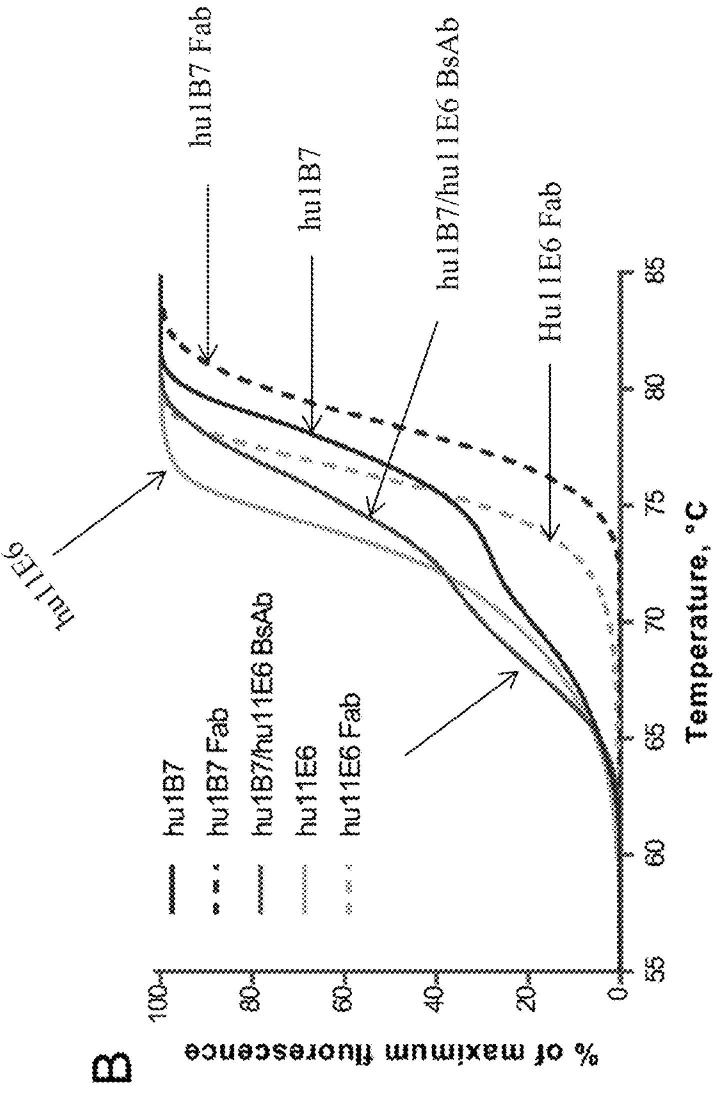

Antibody thermal stability was assessed using a differential scanning fluorimetry assay to monitor protein unfolding. All formats exhibited high stability characteristic of engineered IgG1 antibodies, with melting points of 63° C. or higher in PBS (FIG. 4B). The profiles showed two melting regimes, with the first peak likely representing CH2 unfolding and the second peak representing CH3 and Fab unfolding. For full-length hu1B7, these transitions occurred at 69° C. and 78° C. respectively, while for full-length hu11E6 all domains unfolded around 74° C. The Fab formats showed slightly higher melting temperatures than their full-length counterparts, likely due to a small overall increase in stability without CH2-driven destabilization. The bispecific antibody exhibited a more complex profile, with major transitions at 68° C. and 76° C. The introduction of the knob and hole mutations was expected to have a slight destabilizing effect on the CH3 domain and may be responsible for the decrease in thermal stability of the bispecific, although the melting temperature was still well within the accepted range for therapeutic antibodies.

To assess the PT binding activity of the bispecific antibody and to compare this with the activity of the binary antibody, a series of ELISA assays were performed. To verify that the protein was functionally bispecific, the hu1B7/hu11E6 bispecific and hu1B7H+ and hu11E6H− parent antibodies were compared using a sandwich ELISA (FIG. 5A). The PT-B subunit was used to capture any proteins with the hu11E6 specificity, followed by incubation with S1-220K-biotin and streptavidin-HRP for detection of the hu1B7 specificity. The hu1B7H+ only binds S1-220K-biotin, thus was not bound after the first step; while hu11E6H− binds PT-B but cannot be detected with S1-220K-biotin. In contrast, the bispecific antibody was able to simultaneously bind both PT-B and S1-220K-biotin, exhibiting a characteristic logarithmic binding curve with an EC50 of approximately 4 nM.

The binding characteristics of all individual proteins using a direct PT-binding ELISA were evaluated (FIG. 58). All variants displayed strong binding to PT, with a small shift in EC50 between hu1B7 and hu11E6, consistent with prior data. The bispecific showed a binding profile intermediate to those of the parent antibodies, as expected. While the hu1B7 Fab behaved similarly to full-length hu1B7, the hu11E6 Fab showed a notable increase in EC50 compared to the full-length version. As the pertussis toxin presents two hu11E6 epitopes, this shift could be indicative of an avidity effect favoring the full-length bivalent molecule.

A quantitative competition ELISA was carried to investigate the effective binding affinities of the antibody formats. Specifically, antibody dilutions were incubated with a constant amount of PT, after which unbound antibody was detected by a direct PT233 binding ELISA (FIG. 5C). The equilibrium dissociation constants (KD) was calculated, with corrections for bivalency used for the full-length proteins. The KD values calculated for the full-length hu1B7 and hu11E6 were 0.8±0.1 nM and 6±2 nM respectively. Due to a simple 1:1 interaction with toxin and a more binary "bound" or "not bound" configuration, Fabs are typically used for true affinity measurements. Both the hu1B7 Fab and hu11E6 Fab showed an approximately 3-fold reduction in affinity compared to their full-length parents, with KD values measured as 3.1±0.9 nM and 20±8 nM respectively. The mixture of full-length antibodies and bispecific antibody exhibited effective affinities intermediate to those of the two parents at 2.1±0.8 nM and 1.1±0.4 nM respectively, while the Fab mixture had an effective affinity of 8±4 nM. These affinities were skewed more toward the higher affinity of hu1B7, which in this solution-based assay may capture a larger fraction of available PT molecules than the hu11E6 binding site. The data from these three ELISA assays in aggregate demonstrate that the hu1B7/hu11E6 bispecific was functionally bispecific and behaved similarly to the antibody mixture in a solution-based assay.

Example 4. Neutralization of Pertussis Toxins In Vitro

Methodology

Inhibition of CHO cell clustering was used to determine in vitro neutralization of antibody preparations. Briefly, antibody was serially diluted across a 96-well tissue plate from 200 to ~0.4 nM in the presence of 4 pM PT. Antibody and PT were incubated for 30 minutes at 37° C., after which $1\times10^4$ freshly trypsinized CHO cells were added per well. After incubation at 37° C. for an additional 48 hours, the degree of clustering was scored as 0 (no clustering), 1 (equivocal), 2 (positive clustering), or 3 (maximal clustering). Neutralizing dose is expressed as the lowest molar ratio of antibody:PT resulting in a score of 1. Experiments were performed in triplicate.

Results

The neutralization capacity of the hu1B7/hu11E6 bispecific antibody was assessed in an in vitro model. Specifically, a CHO cell assay was used method to quantify PT activity and neutralization by observing morphological changes in CHO-K1 cells after incubation with toxin or toxin plus antibody.

Figure 6:
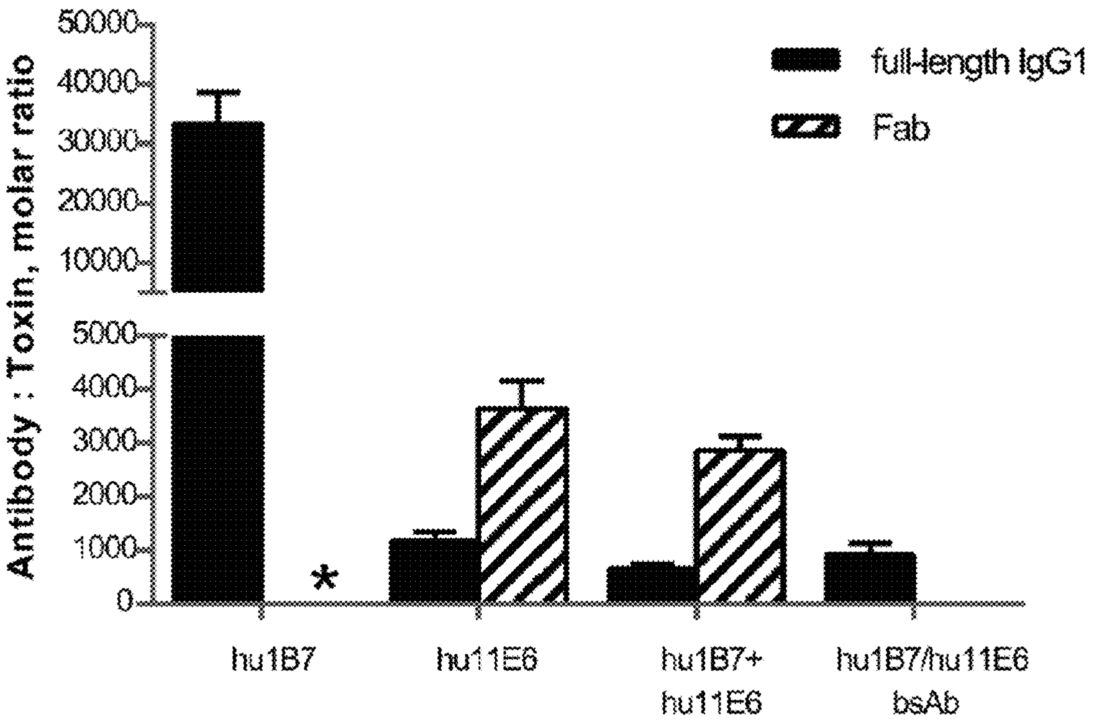
FIG. 6 shows in vitro PT neutralization by the bispecific antibody as measured by inhibition of CHO cell clustering. Adherent CHO-K1 cells were grown in the presence of 4 pM PT pre-equilibrated with antibody dilutions. The lowest molar ratio of antibody:toxin that was able to fully prevent clustering was recorded as the neutralizing ratio. Data shown for neutralization with the full-length antibodies (solid bars) and Fab fragments (striped bars). Error bars represent standard deviation of 6 replicates over three experiments. No neutralization was observed for the hu1B7 Fab under these conditions.

A constant amount of PT (4 pM) was incubated with a series of antibody concentrations (molar excess of 50,000 to 1,000) in a 96-well plate. CHO-K1 cells were seeded into the wells and incubated for 48 hours, prior to scoring for the degree of cell clustering. Here the neutralizing ratio was reported as the lowest molar ratio of antibody of toxin which was able to completely prevent the clustered morphology, a score of 1 on the established 0 to 3 scale (FIG. 6). Full length hu11E6 and hu1B7 were able to completely neutralize the toxin at a ~1,100:1 and ~34,000:1 ratio respectively. The fact that hu1B7 performed poorly in this assay despite superior performance in a mouse aerosol challenge model was not surprising, given prior reports showing that CHO cell clustering was not a good predictor of protection in vivo. The hu1B7+hu11E6 mixture and hu1B7/hu11E6 bispecific were also able to fully neutralize the toxin, with antibody:PT ratios of ~700:1 and ~900:1 respectively. These values were similar to the value for hu11E6 alone, despite having only half the concentration of hu11E6 binding arms in the mixture or bispecific formulation. This suggested that the bispecific format did not compromise activity of hu11E6 and the presence of hu1B7 contributed to full toxin neutralization. These data suggested synergy with the bispecific antibody.

The hu1B7 and hu11E6 Fabs as well as a mixture of the two were used to assess the role of valency in PT neutralization. In general the Fabs required approximately 3 fold more protein to achieve the same neutralization as the full length antibodies (3,600:1 for hu11E6 Fab, 2,900:1 for Fab mix; FIG. 6) in this in vitro assay in which molecule size and serum half-life were not expected to matter. Neutralization using the hu1B7 Fab was not detected under these stringent assay conditions. These results correlated well with the reduction in affinity seen with the Fabs in the competition ELISA. Moreover, the superior performance of the intact immunoglobulins suggests that either the avidity effects afforded by bivalency or the ability of a bivalent molecule to cross-link two PT molecules was crucial for PT neutralization.

Example 5. Bispecific Antibodies Synergistically Inhibited PT-Induced Leukocytosis In Vivo Methodology An in vivo leukocytosis assay has been previously described, and was performed with the following modifications. First, 2 μg PT or 2 μg PT plus 20 μg of antibody were pre-incubated for two hours at room temperature to allow for binding equilibration. These preparations were then injected into a lateral tail vein of 5-6 week old female BALB/c mice. Four days later, blood was collected by terminal cardiac puncture and combined with $Na_2EDTA$ to a final concentration of 10 mM to prevent clotting. Blood (10 μl) was lysed in 150 μl mouse red blood cell lysis buffer (Alfa Aesar) for 15 minutes, washed with PBS+2% FBS, and stained for one hour on ice with 5 μg/mL anti-mouse CD45 antibody or isotype control antibody, each labeled with Alexa Fluor 488 (BioLegend). Samples were run on a flow cytometer (BD LSR-Fortessa) with CountBright absolute counting beads (Life Technologies) to calculate the total number of white blood cells (WBC) per μl blood. Group sizes were based on power calculations from pilot experiment data, with groups of 6 (PBS) or 10-11 (PTx and antibody treated) mice per group. Statistical analysis was performed using a 1-way ANOVA and Tukey's test.

Results

Systemic leukocytosis is a primary outcome of *B. pertussis* infection and is predictive of severe disease in humans. To better assess the therapeutic potential of the hu1B7/hu11E6 bispecific antibody, an in vivo leukocytosis assay was utilized which measures the ability of an antibody to neutralize the increase in white blood cell (WBC) count induced by the injection of purified pertussis toxin. This assay has previously been shown to be more predictive of protection during bacterial infection than the CHO cell assay.

FIG. 7A shows the white blood cell count (WBC) of mice treated with 200 μg purified hu1B7 or PBS. As indicated antibody treatment alone does not affect WBC. Juvenile BALB/c mice were injected with pre-equilibrated mixtures of 20 μg of the full-length antibody and 2 μg the toxin or toxin alone. Four days later, whole blood was collected and assayed for white blood cells by staining for CD45 and measuring fluorescent cells via flow cytometry (FIG. 7B). The toxin alone induced a 10-20 fold increase in WBC as compared to PBS treated mice, while the full-length hu1B7 and hu11E6 antibodies were each able to significantly reduce this WBC rise ($p<0.0001$ and $p<0.01$, respectively). Of these, hu1B7 was significantly more effective than hu11E6 ($p<0.001$), consistent with previous data showing enhanced in vivo protection against bacterial challenge by hu1B7. The same dose of control antibody alone did not cause a change in WBC count (data not shown). Additionally, a cocktail of hu1B7 and hu11E6 antibodies were synergistic in reducing the rise in WBC. The bi-specific antibody also synergistically reduced the rise in WBC (FIG. 7B).

To allow for the detection of synergy, the relatively low ratio of 20 μg of total antibody per 2 μg of toxin was selected based on pilot experiments demonstrating that this dose only partially suppressed the WBC count (data not shown). Under these conditions, an equimolar antibody mixture (10 μg each antibody) exhibited a significant improvement over treatment with the same dose of either hu1B7 or hu11E6 alone (20 μg antibody; $p<0.0001$). The resulting WBC count was not significantly different than that for PBS-treated mice that were not exposed to PT. Since the antibody mixture contains equimolar amounts of both the hu1B7 and hu11E6 specificity, it was expected to behave as a linear combination of the two. Instead, the efficacy of the mix was significantly enhanced over either of the monoclonal preparations, which was indicative of synergy. Treatment with 20 μg of the bispecific antibody also significantly reduced the WBC as compared to the monoclonal preparations ($p<0.01$ vs hu1B7, $p<0.0001$ vs hu11E6). Notably, there was no difference between WBC for mice treated with the antibody mixture as compared to those treated with the bispecific antibody at this level. This showed that the bispecific antibody was able to capture the synergy observed in the mixture of the two antibodies. Without wishing to be bound by theory, it is believed that synergy is achieved by neutralization of both the A and B subunits as provided by the bispecific antibody. The antibody mixture was also previously shown to be effective in both murine prophylactic and weanling baboon therapeutic models, and as the antibody mixture and bispecific antibody perform similarly in the current murine toxin challenge model, it is expected that the bispecific antibody can recapitulate the efficacy of the mixture in an infection experiment.

Example 6. Evaluation of the Bispecific Antibodies in Treating *B. pertussis* Infections in Baboons The efficacy of the hu1B7/hu11E6 bispecific antibody in treating *B. pertussis* infections is evaluated in a baboon model.

Specifically, weanling (6-9 month old) male and female baboons (*Papio anubus*, olive baboons) of about 2-3 kg in weight are infected by intranasal administration of the *B. pertussis* D420 strain and treated intravenously with the hu1B7/hu11E6 bispecific antibody. The infected baboons are analyzed for clinical signs of illness (for example, coughing, weight and temperature), white blood cell counts, and/or nasal carriage levels of *B. pertussis.*

For the *B. pertussis* infection, a *B. pertussis* strain, D420, is suspended in PBS at $10^9$-$10^{10}$ cfu/ml. One ml is delivered via endrotracheal tube to the top of the baboon trachea. 0.5 ml is delivered via an intranasal catheter to the back of each naris. Baboons are then placed in a sitting position for 3 minutes. For the phlebotomy, <5 ml of blood is collected via venipuncture with a butterfly catheter and is aliquoted into tubes for white blood cell determination and serum separation. Throughout the study, the baboons are anesthetized with an intramuscular injection of ketamine for activities including antibody infusions, *B. pertussis* infection, blood draws, nasopharyngeal washes, and clinical observations. These activities are combined whenever possible to minimize the use of anesthesia.

Two studies are conducted. In one, three baboons are each infected with $6\times10^9$ CFU of *B. pertussis*. Three days later, two of the animals are treated with the hu1B7/hu11E6 bispecific antibody, and the third animal remains untreated. Three weeks after infection, the animals are euthanized. Histological evaluations of lung sections are performed. In the second study, four baboons are infected with $4\times10^9$ CFU of *B. pertussis* and three days later, two of the animals are treated with the hu1B7/hu11E6 bispecific antibody, and two animals remain untreated. The antibodies are administered via intravenous injection.

It is expected that untreated animals will develop severe leukocytosis which persists until the animals become moribund. In contrast, the animals treated with the hu1B7/hu11E6 bispecific antibody become healthy following antibody administration. Specifically, in the treated animals, the white blood cell counts as well as cough counts will decrease until they normalize. Similarly, the *B. pertussis* bacterial cell counts in the nasal washes also demonstrates a similar decline for the hu1B7/hu11E6 bispecific antibody-treated animals, while the bacterial counts in the nose of the two control animals remain pathologically high.

Additionally, the hu1B7/hu11E6 bispecific antibody also mitigates pulmonary bacterial burden in the treated animals. For example, at necropsy, the untreated animal is shown to have a consolidated right lung. Histopathology of this lung demonstrates severe subacute to chronic, diffuse interstitial pneumonia with abscess formation and moderate interstitial fibrosis. There also is moderate chronic multifocal organizing pleuritis with an area of abscess formation. In contrast, at necropsy, the lungs of the treated animals are expected to be grossly normal. Thus, the untreated animal demonstrates changes of severe pneumonia, whereas the lungs of the treated animals are normal.

These data supports the clinical application of the hu1B7/hu11E6 bispecific antibodies of the invention as a means to diminish morbidity, long-term sequelae, and mortality in children with pertussis.

Example 7. Prophylactic Administration of Bispecific Antibodies to Newborns

The hu1B7/hu11E6 bispecific antibodies are administered via intramuscular injection to newborns to provide prophylactic treatment against pertussis via passive immunization. Since pertussis during the first four months of life portends the highest risk for death or serious illness with long-term sequelae, treatment at birth can protect children during this high risk period and/or until they are old enough to receive a standard pertussis vaccine. This may be particularly important in the developing world where the risk of contracting pertussis is high, the disease kills 160,000 to 300,000 children annually, and newborns only see a physician once at birth.

The hu1B7/hu11E6 bispecific antibodies are expected to provide at least four months of prophylaxis due to its plasma half-life and potency.

The potency of the hu1B7/hu11E6 bispecific antibodies is assessed vis-à-vis the World Health Organization's (WHO's) polyclonal serum standard routinely used to predict vaccine efficacy. The WHO potency is quantified in equivalent units (EU), and 5 EU/ml is considered a protective level in humans. See Storsaeter J. et al. (1998), Vaccine, 16(20):1907-16. The potency of the hu1B7/hu11E6 bispecific antibodies is expected to be greater than 5 EU/ml.

INCORPORATION BY REFERENCE

The entire disclosure of each of the patent documents and scientific articles referred to herein is incorporated by reference for all purposes.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A bispecific antibody that binds a pertussis toxin protein, comprising an immunoglobulin heavy chain and light chain of a humanized 1B7 antibody, wherein the immunoglobulin heavy chain derived from the humanized 1B7 antibody comprises a $CDR_{H1}$ comprising an amino acid sequence of SEQ ID NO: 1, a $CDR_{H2}$ comprising an amino acid sequence of SEQ ID NO:2, and a $CDR_{H3}$ comprising an amino acid sequence of SEQ ID NO: 3; and the immunoglobulin light chain derived from the humanized 1B7 antibody comprises a $CDR_{L1}$ comprising an amino acid sequence of SEQ ID NO: 6, a $CDR_{L2}$ comprising an amino acid sequence of SEQ ID NO: 7, and a $CDR_{L3}$ comprising an amino acid sequence of SEQ ID NO: 8; and an immunoglobulin heavy chain and light chain of a humanized 11E6 antibody, wherein the immunoglobulin heavy chain derived from the humanized 11E6 antibody comprises a $CDR_{H1}$ comprising an amino acid sequence of SEQ ID NO: 11, a $CDR_{H2}$ comprising an amino acid sequence of SEQ ID NO: 12, and a $CDR_{H3}$ comprising an amino acid sequence of SEQ ID NO: 13; and the immunoglobulin light chain derived from the humanized 11E6 antibody comprises a $CDR_{L1}$ comprising an amino acid sequence of SEQ ID NO: 16, a $CDR_L2$ comprising an amino acid sequence of SEQ ID NO: 17, and a $CDR_L3$ comprising an amino acid sequence of SEQ ID NO: 18, wherein the immunoglobulin heavy chain derived from the humanized 1B7 antibody comprises a mutation at T366, numbered according to the EU index as in Kabat and wherein the immunoglobulin heavy chain derived from the humanized 11E6 antibody comprises a mutation at Y407, numbered according to the EU index as in Kabat.

2. The bispecific antibody of claim 1, wherein the immunoglobulin heavy chain derived from the humanized 1B7 antibody comprises a heavy chain variable region comprising an amino acid sequence having at least 70% sequence identity with SEQ ID NO: 4; and the immunoglobulin light chain derived from the humanized 1B7 antibody comprises a light chain variable region comprising an amino acid sequence having at least 70% sequence identity with SEQ ID NO: 9.

3. The bispecific antibody of claim 1, wherein the immunoglobulin heavy chain derived from the humanized 1B7 antibody comprises an amino acid sequence having at least 70% sequence identity with SEQ ID NO:5, and the immunoglobulin light chain derived from the humanized 1B7 antibody comprises an amino acid sequence having at least 70% sequence identity with SEQ ID NO: 10.

4. The bispecific antibody of claim 1, where the mutation at T366 is T366Y.

5. The bispecific antibody of claim 1, wherein the immunoglobulin heavy chain derived from the humanized 11E6 antibody comprises a heavy chain variable region comprising an amino acid sequence having at least 70% sequence identity with SEQ ID NO: 14; and the immunoglobulin light chain derived from the humanized 11E6 antibody comprises a light chain variable region comprising an amino acid sequence having at least 70% sequence identity with SEQ ID NO: 19.

6. The bispecific antibody of claim 1, wherein the immunoglobulin heavy chain derived from the humanized 11E6 antibody comprises an amino acid sequence having at least 70% sequence identity with SEQ ID NO: 15, and the immunoglobulin light chain derived from the humanized 11E6 antibody comprises an amino acid sequence having at least 70% sequence identity with SEQ ID NO: 20.

7. The bispecific antibody of claim 1, where the mutation at Y407 is Y407T.

8. A pharmaceutical composition comprising the bispecific antibody of claim 1, and a pharmaceutically acceptable excipient.

9. A method of treating a patient infected with *Bordetella pertussis*, comprising administering to the patient the bispecific antibody of claim 1.

10. A method of preventing pertussis in a subject previously exposed to *Bordetella pertussis*, comprising administering to the subject the bispecific antibody of claim 1.

* * * * *

SEQUENCE LISTING

```
<160> NUMBER OF SEQ ID NOS: 21

<210> SEQ ID NO 1
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1

Gly Tyr Lys Phe Thr Ser Tyr Trp Met His
1               5                   10


<210> SEQ ID NO 2
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 2

Asn Ile Phe Pro Gly Ser Gly Ser Thr Asn Tyr Ala Gln Lys Phe Gln
1               5                   10                  15

Gly


<210> SEQ ID NO 3
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 3

Trp Leu Ser Gly Ala Tyr Phe Asp Tyr
1               5
```

<210> SEQ ID NO 4
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 4

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Trp Met His Trp Val Arg Gln Ala Pro Gly Gln Gly Leu Glu Trp Ile
        35                  40                  45

Gly Asn Ile Phe Pro Gly Ser Gly Ser Thr Asn Tyr Ala Gln Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Leu Ser Gly Ala Tyr Phe Asp Tyr Trp Gly Gln Gly Thr
            100                 105                 110

Thr Val Thr Val Ser Ser
        115
```

<210> SEQ ID NO 5
<211> LENGTH: 467
<212> TYPE: PRT
<213> ORGANISM: Artificial sequence
<220> FEATURE:
<223> OTHER INFORMATION: Synthetic polypeptide

<400> SEQUENCE: 5

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Lys Phe
        35                  40                  45

Thr Ser Tyr Trp Met His Trp Val Arg Gln Ala Pro Gly Gln Gly Leu
    50                  55                  60

Glu Trp Ile Gly Asn Ile Phe Pro Gly Ser Gly Ser Thr Asn Tyr Ala
65                  70                  75                  80

Gln Lys Phe Gln Gly Arg Val Thr Leu Thr Val Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Trp Leu Ser Gly Ala Tyr Phe Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
```

-continued

```
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Tyr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 6
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 6

Ser Ala Ser Ser Ser Val Ser Phe Met Tyr
1               5                   10


<210> SEQ ID NO 7
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 7
```

Leu Thr Ser Asn Leu Pro Ser
1 5

<210> SEQ ID NO 8
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 8

Gln Gln Trp Ser Ser His Pro Pro Thr
1 5

<210> SEQ ID NO 9
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 9

```
Gln Ile Val Leu Thr Gln Ser Pro Ala Thr Leu Ser Val Ser Pro Gly
1               5                   10                  15

Glu Arg Val Thr Leu Thr Cys Ser Ala Ser Ser Ser Val Ser Phe Met
            20                  25                  30

Tyr Trp Tyr Gln Gln Lys Pro Gly Arg Ala Pro Lys Pro Leu Ile Tyr
        35                  40                  45

Leu Thr Ser Asn Leu Pro Ser Gly Val Pro Ala Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys Gln Gln Trp Ser Ser His Pro Pro Thr
                85                  90                  95

Phe Gly Ser Gly Thr Lys Leu Glu Ile Lys
            100                 105
```

<210> SEQ ID NO 10
<211> LENGTH: 232
<212> TYPE: PRT
<213> ORGANISM: Artificial sequence
<220> FEATURE:
<223> OTHER INFORMATION: Synthetic polypeptide

<400> SEQUENCE: 10

```
Met Gly Trp Ser Cys Ile Ile Leu Phe Leu Val Ala Thr Ala Thr Gly
1               5                   10                  15

Val His Ser Gln Ile Val Leu Thr Gln Ser Pro Ala Thr Leu Ser Val
            20                  25                  30

Ser Pro Gly Glu Arg Val Thr Leu Thr Cys Ser Ala Ser Ser Ser Val
        35                  40                  45

Ser Phe Met Tyr Trp Tyr Gln Gln Lys Pro Gly Arg Ala Pro Lys Pro
    50                  55                  60

Leu Ile Tyr Leu Thr Ser Asn Leu Pro Ser Gly Val Pro Ala Arg Phe
65                  70                  75                  80

Ser Gly Ser Gly Ser Gly Thr Ser Tyr Thr Leu Thr Ile Asn Ser Leu
                85                  90                  95

Glu Ala Glu Asp Ala Ala Thr Tyr Tyr Cys Gln Gln Trp Ser Ser His
            100                 105                 110

Pro Pro Thr Phe Gly Ser Gly Thr Lys Leu Glu Ile Lys Arg Thr Val
```

115 120 125

Ala Ala Pro Ser Val Phe Ile Phe Pro Pro Ser Asp Glu Gln Leu Lys
130 135 140

Ser Gly Thr Ala Ser Val Val Cys Leu Leu Asn Asn Phe Tyr Pro Arg
145 150 155 160

Glu Ala Lys Val Gln Trp Lys Val Asp Asn Ala Leu Gln Ser Gly Asn
165 170 175

Ser Gln Glu Ser Val Thr Glu Gln Asp Ser Lys Asp Ser Thr Tyr Ser
180 185 190

Leu Ser Ser Thr Leu Thr Leu Ser Lys Ala Asp Tyr Glu Lys His Lys
195 200 205

Val Tyr Ala Cys Glu Val Thr His Gln Gly Leu Ser Ser Pro Val Thr
210 215 220

Lys Ser Phe Asn Arg Gly Glu Cys
225 230

<210> SEQ ID NO 11
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 11

Gly Phe Thr Phe Thr Asp Tyr Tyr Val Ser
1 5 10

<210> SEQ ID NO 12
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 12

Phe Ile Arg Asn Lys Val Asn Gly Tyr Thr Thr Glu Phe Ser Ser Ser
1 5 10 15

Val Lys Gly

<210> SEQ ID NO 13
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 13

Val Ser Tyr Tyr Gly Arg Gly Trp Tyr Phe Asp Tyr
1 5 10

<210> SEQ ID NO 14
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 14

Glu Val Gln Val Val Glu Ser Gly Gly Gly Leu Val Gln Pro Gly Arg
1 5 10 15

Ser Leu Arg Leu Ser Cys Thr Thr Ser Gly Phe Thr Phe Thr Asp Tyr
20 25 30

Tyr Val Ser Trp Val Arg Gln Ala Pro Gly Lys Ala Leu Glu Trp Leu
35 40 45

Gly Phe Ile Arg Asn Lys Val Asn Gly Tyr Thr Thr Glu Phe Ser Ser
50 55 60

Ser Val Lys Gly Arg Phe Thr Ile Ser Arg Asp Asn Ser Lys Ser Ile
65 70 75 80

Leu Tyr Leu Gln Met Asn Ser Leu Lys Ile Glu Asp Thr Ala Val Tyr
85 90 95

Tyr Cys Ala Arg Val Ser Tyr Tyr Gly Arg Gly Trp Tyr Phe Asp Tyr
100 105 110

Trp Gly Gln Gly Thr Thr Leu Thr Val Ser Ser
115 120

<210> SEQ ID NO 15
<211> LENGTH: 472
<212> TYPE: PRT
<213> ORGANISM: Artificial sequence
<220> FEATURE:
<223> OTHER INFORMATION: Synthetic polypeptide

<400> SEQUENCE: 15

Met Gly Trp Ser Cys Ile Ile Leu Phe Leu Val Ala Thr Ala Thr Gly
1 5 10 15

Val His Ser Glu Val Gln Val Val Glu Ser Gly Gly Gly Leu Val Gln
20 25 30

Pro Gly Arg Ser Leu Arg Leu Ser Cys Thr Thr Ser Gly Phe Thr Phe
35 40 45

Thr Asp Tyr Tyr Val Ser Trp Val Arg Gln Ala Pro Gly Lys Ala Leu
50 55 60

Glu Trp Leu Gly Phe Ile Arg Asn Lys Val Asn Gly Tyr Thr Thr Glu
65 70 75 80

Phe Ser Ser Ser Val Lys Gly Arg Phe Thr Ile Ser Arg Asp Asn Ser
85 90 95

Lys Ser Ile Leu Tyr Leu Gln Met Asn Ser Leu Lys Ile Glu Asp Thr
100 105 110

Ala Val Tyr Tyr Cys Ala Arg Val Ser Tyr Tyr Gly Arg Gly Trp Tyr
115 120 125

Phe Asp Tyr Trp Gly Gln Gly Thr Thr Leu Thr Val Ser Ser Ala Ser
130 135 140

Thr Lys Gly Pro Ser Val Phe Pro Leu Ala Pro Ser Ser Lys Ser Thr
145 150 155 160

Ser Gly Gly Thr Ala Ala Leu Gly Cys Leu Val Lys Asp Tyr Phe Pro
165 170 175

Glu Pro Val Thr Val Ser Trp Asn Ser Gly Ala Leu Thr Ser Gly Val
180 185 190

His Thr Phe Pro Ala Val Leu Gln Ser Ser Gly Leu Tyr Ser Leu Ser
195 200 205

Ser Val Val Thr Val Pro Ser Ser Ser Leu Gly Thr Gln Thr Tyr Ile
210 215 220

Cys Asn Val Asn His Lys Pro Ser Asn Thr Lys Val Asp Lys Lys Val
225 230 235 240

Glu Pro Lys Ser Cys Asp Lys Thr His Thr Cys Pro Pro Cys Pro Ala
245 250 255

Pro Glu Leu Leu Gly Gly Pro Ser Val Phe Leu Phe Pro Pro Lys Pro
260 265 270

-continued

```
Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Thr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470


<210> SEQ ID NO 16
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 16

Arg Ala Ser Gln Asp Ile Asp Asn Tyr Leu Ser
1               5                   10


<210> SEQ ID NO 17
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 17

Tyr Thr Ser Arg Leu His Ser
1               5


<210> SEQ ID NO 18
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 18

Gln Gln Gly Asn Thr Phe Pro Trp Thr
1               5
```

<210> SEQ ID NO 19
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 19

```
Asp Ile Val Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Ser Trp Phe Gln Gln Lys Pro Gly Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys
            100                 105
```

<210> SEQ ID NO 20
<211> LENGTH: 233
<212> TYPE: PRT
<213> ORGANISM: Artificial sequence
<220> FEATURE:
<223> OTHER INFORMATION: Synthetic polypeptide

<400> SEQUENCE: 20

```
Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Ser Ala
            20                  25                  30

Ser Val Gly Asp Arg Val Thr Ile Ser Cys Arg Ala Ser Gln Asp Ile
        35                  40                  45

Asp Asn Tyr Leu Ser Trp Phe Gln Gln Lys Pro Gly Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Thr Leu Thr Ile Ser Ser
                85                  90                  95

Leu Gln Pro Glu Asp Ile Ala Thr Tyr Phe Cys Gln Gln Gly Asn Thr
            100                 105                 110

Phe Pro Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205
```

-continued

```
Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 21
<211> LENGTH: 232
<212> TYPE: PRT
<213> ORGANISM: Artificial sequence
<220> FEATURE:
<223> OTHER INFORMATION: Synthetic polypeptide

<400> SEQUENCE: 21

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```